Figure 1:
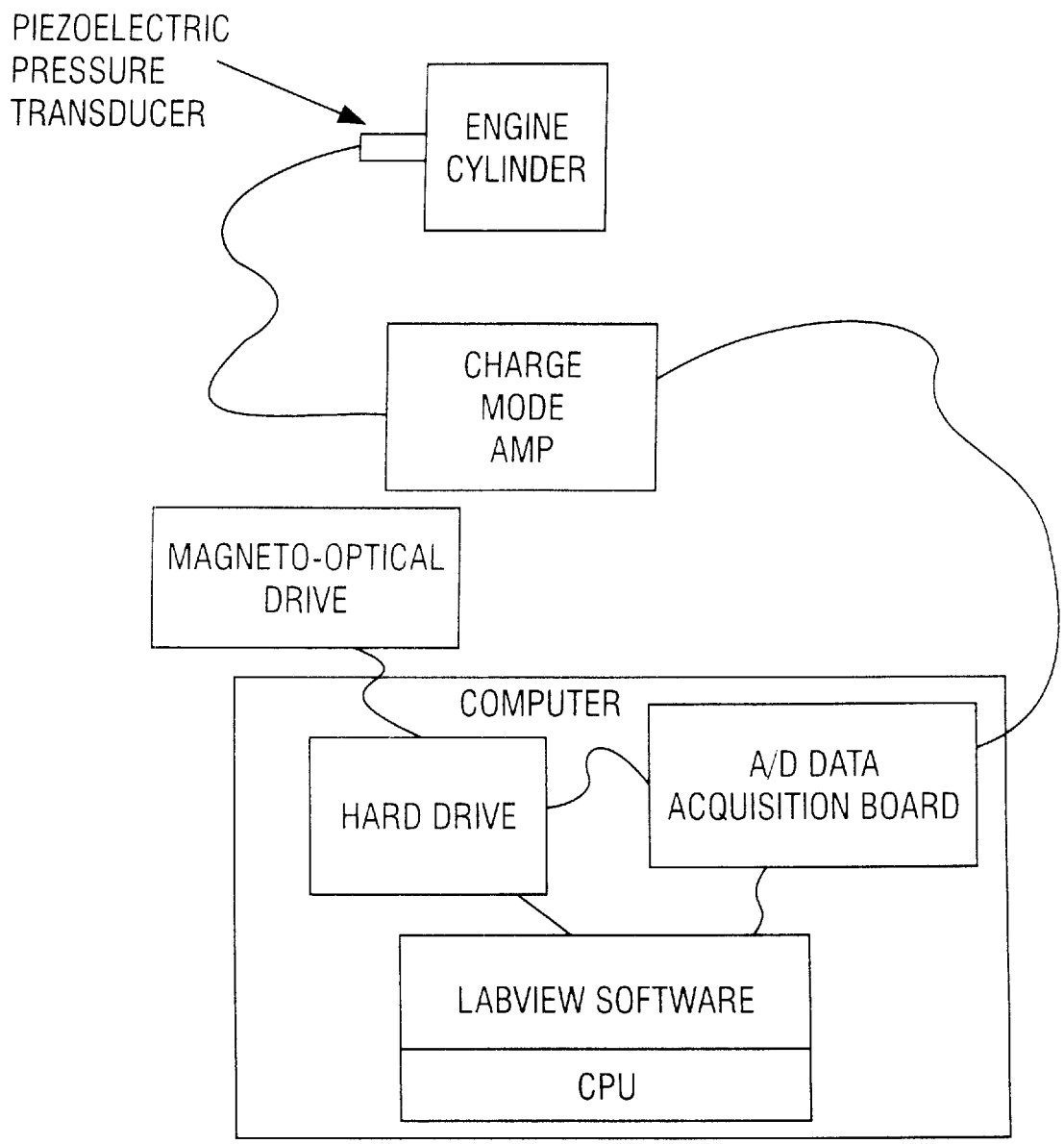

United States Patent [19]

Liiva et al.

[11] Patent Number: 5,962,775

[45] Date of Patent: Oct. 5, 1999

[54] METHOD FOR TESTING UNLEADED AVIATION GASOLINES

[75] Inventors: Peter M. Liiva, Greenwich, Conn.; Joseph N. Valentine, Newburgh, N.Y.; Teddy G. Campbell, Brookfield, Conn.

[73] Assignee: Texaco, Inc.

[21] Appl. No.: 08/856,197

[22] Filed: May 14, 1997

Related U.S. Application Data

[60] Provisional application No. 60/018,254, May 24, 1996.

[51] Int. Cl.[6] .................................................. G01N 33/22
[52] U.S. Cl. ............................................................ 73/35.02
[58] Field of Search ......................... 73/35, 35.06, 35.02, 73/35.13, 35.12; 123/516; 235/151.35; 44/426

[56] References Cited

U.S. PATENT DOCUMENTS

| | | | |
|---|---|---|---|
| 2,819,953 | 1/1958 | Brown et al. | 44/74 |
| 3,318,136 | 5/1967 | Payne et al. | 73/35 |
| 4,010,358 | 3/1977 | Morris | 235/151.35 |
| 4,233,035 | 11/1980 | Allen et al. | 44/73 |
| 4,396,398 | 8/1983 | Knight | 44/56 |
| 4,405,338 | 9/1983 | Jenkins, Jr. et al. | 44/78 |
| 5,470,358 | 11/1995 | Gaughan | 44/426 |
| 5,484,463 | 1/1996 | Cherpeck | 44/387 |
| 5,514,190 | 5/1996 | Cunningham et al. | 44/415 |
| 5,516,342 | 5/1996 | Cherpeck | 44/347 |
| 5,581,016 | 12/1996 | Gonzalez et al. | 73/35.06 |

FOREIGN PATENT DOCUMENTS

WO94/25545  11/1994  WIPO.

OTHER PUBLICATIONS

Valentine et al., "Developing a High Octane Unleaded Aviation Gasoline," *SAE International Meeting & Exposition* (1997).

*Primary Examiner*—Hezron Williams
*Assistant Examiner*—Thuy Vinh Tran
*Attorney, Agent, or Firm*—Arnold, White & Durkee

[57] ABSTRACT

A method for testing an unleaded aviation gasoline (Avgas) composition involves (a) running an aviation engine such as a Textron Lycoming IO-360 engine with an Avgas at maximum knocking conditions, (b) collecting pressure trace data of continuous engine cycles with pressure transducers attached to the cylinders, (c) filtering and transforming the data, and (d) determining the number of knocking cycles and intensity within a predetermined number of continuous engine cycles.

6 Claims, 30 Drawing Sheets

METHOD FOR TESTING UNLEADED AVIATION GASOLINES

This application claims benefit of Provisional Appl. 60/018,254, filed May 24, 1996.

BACKGROUND OF THE INVENTION

The present invention relates generally to methods for testing aviation gasoline (Avgas) compositions. More particularly, the present invention concerns a method for testing unleaded Avgas compositions for use in piston-driven aircraft engines by determining the knocking cycles and intensity in the engine performing at maximum knocking conditions.

Conventional aviation gasoline (Avgas) generally contains an aviation alkylate basefuel and a lead-based additive package. The industry standard Avgas known as 100 Low Lead (100LL) contains the lead additive tetraethyllead (TEL) for boosting the anti-knock property of the Avgas over the inherent anti-knock property of its aviation alkylate basefuel. Knocking is a condition of piston-driven aviation engines due to autoignition, the spontaneous ignition of endgases (gases trapped between the cylinder wall and the approaching flame front) in an engine cylinder after the sparkplug fires. A standard test that has been applied to measure the anti-knock property of lead-based Avgas under various conditions is the motor octane number (MON) rating test (ASTM D2700). Another standard test applied to lead-based Avgas is the supercharge (performance number) rating test (ASTM D909).

Despite the ability of lead-based Avgas to provide good anti-knock property under the severe demands of piston-driven aviation engines, such lead-based compositions are meeting stricter regulations due to their lead and lead oxide emissions. Current U.S. regulations set a maximum amount of TEL for aviation fuels at 4.0 ml/gal and concerns for the negative environmental and health impact of lead and lead oxide emissions may effect further restrictions.

Gaughan (PCT/US94/04985, U.S. Pat. No. 5,470,358) refers to a no-lead Avgas containing an aviation basefuel and an aromatic amine additive. The Avgas compositions exemplified in Gaughan contain an aviation basefuel (e.g., isopentane, alkylate and toluene) having a MON of 92.6 and an alkyl- or halogen-substituted phenylamine that boosts the MON to at least about 98.

The MON and supercharge rating tests, however, were designed at a time when leaded Avgas was the industry standard. In light of newly developed unleaded Avgases, the MON and supercharge rating tests may no longer be the best available method for determining the performance of Avgas compositions. Such determinations are important due to the demands of piston-aircraft engines operating at high power outputs for long periods of time.

Therefore, it would be desirable to find alternative methods for testing unleaded Avgas compositions.

SUMMARY OF THE INVENTION

The inventive method for testing unleaded Avgas compositions for use in piston-driven aircraft engines involves (a) running a Textron Lycoming IO-360 engine with the subject Avgas at maximum knocking conditions, (b) collecting pressure traces of continuous engine cycles with pressure transducers attached to the cylinders, (c) filtering and transforming the data with an algorithm process and (d) determining the number of knocking cycles and knocking intensity within a predetermined number of continuous engine cycles.

The invention is further directed to novel Avgas compositions identified by the above method for testing Avgas compositions that have minimal autoignition in a piston-driven aircraft engine at maximum potential knocking conditions.

DESCRIPTION OF ILLUSTRATIVE EMBODIMENTS

For purposes of the invention, "Avgas" or "Avgas composition" refers to an aviation gasoline. In general, an Avgas is a blend made of a basefuel composition and one or more additives.

EXAMPLES

Various Avgas compositions were tested in MON, supercharge and Knock Cycles/Intensity rating tests. The results indicated that MON and supercharge ratings may not be sufficient for predicting the performance of an unleaded Avgas and that the inventive Knock Cycles/Intensity rating is a better predictor of Avgas performance and a better means for identifying good Avgas compositions.

Examples

A. Determination of MON

The MON rating test (ASTM D2700) is conducted using a single cylinder variable-compression laboratory engine which has been calibrated with reference fuels of defined octane levels. The sample of interest is compared to two reference fuels at standard knock intensity and the octane number of the sample is determined by bracketing or compression ratio (c.r.) methods. In bracketing, the octane value of the sample is determined by interpolating between two reference fuel octane values. In the c.r. method, the octane value of the sample is determined by finding the compression ratio which duplicates the standard knock intensity of a reference fuel and the octane number is then found in a table of values. Repeatability limits for MON determination at 95% confidence intervals is 0.3 MON for 85–90 MON fuels while reproducibility limits are 0.9 for 85 MON and 1.1 for 90 MON.

B. Determination of Supercharge Rating

The Supercharge rating test (ASTM-D909) determines the knock-limited power, under supercharge rich-mixture conditions, of fuels for use in spark ignition reciprocating aircraft engines. The Supercharge rating is an industry standard for testing the severe octane requirements of piston driven aircraft. For purposes of this application, "ASTM-D909" is used interchangeably with both "supercharge rating" and "performance number."

C. Determination of Knock Cycles and Intensity Rating

For purposes of this application, "Knock Cycle/Intensity rating test" and "Lycoming IO-360 tests" are used interchangeably. The Knock Cycles/Intensity rating test was performed with a Textron Lycoming IO-360 engine ("the Lycoming engine") on a dynamometer test stand (See FIG. 1). Each of the four cylinders of the Lycoming engine was equipped with a Kistler 6061B piezoelectric transducer. These transducers produce electric charges proportional to the detected pressures in the combustion chambers in the Lycoming Engine. The charge was then passed into four Kistler 5010 charge mode amplifiers which were calibrated so that output voltage from the amplifiers was equivalent to 20 atmospheres as read by the detector. The voltage was processed through a National Instruments NB-A2000 A/D board which reads all four channels simultaneously at a rate of 250,000 samples per second at a resolution of 12 bits.

Figure 2:
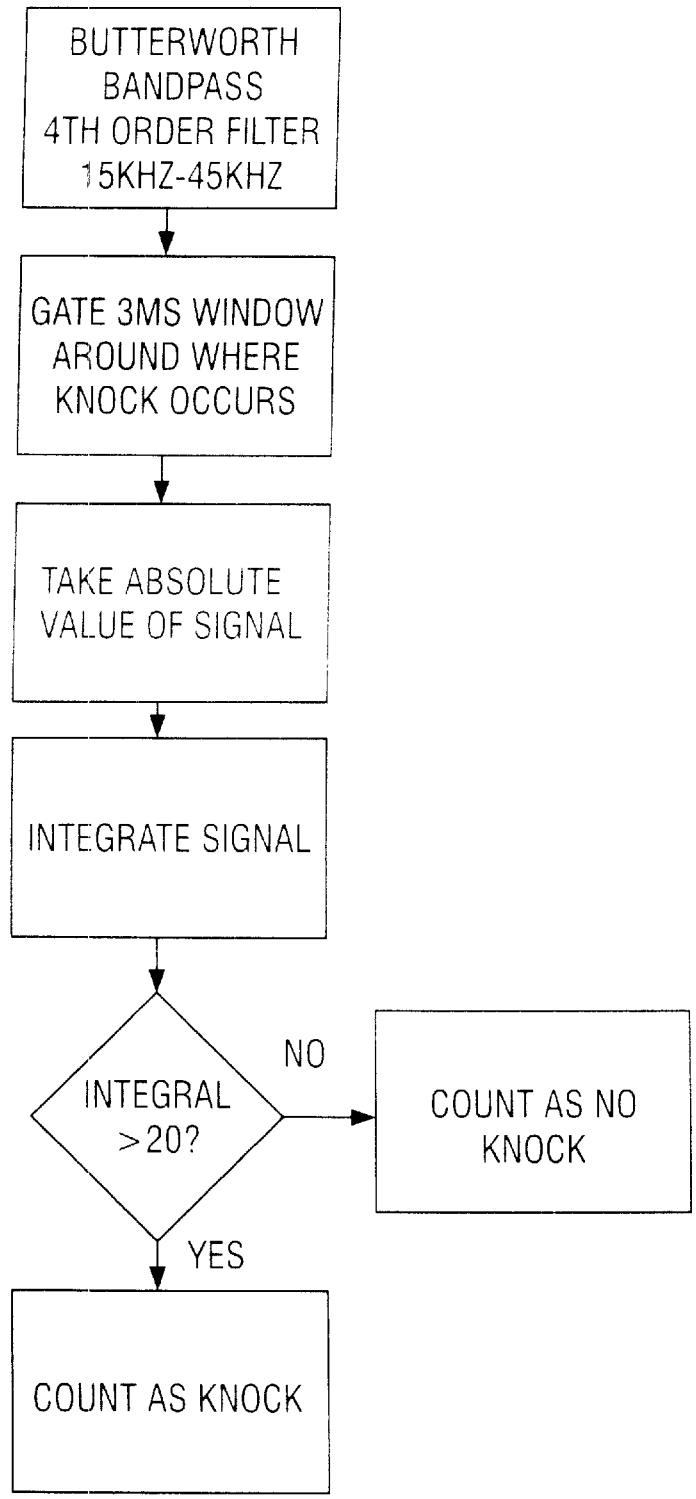

The data acquisition was facilitated by a computer program (See FIG. 2) using National Instruments' Labview programming environment. The data acquisition program stores the data from 200 to 400 consecutive firings from the engine which is typically operated at 2700 rpm, wide open throttle at an equivalence ratio of about 1.12 and maximum cylinder temperature of just below 500° F. The data is first stored into buffers, then into the Random Access Memory of a MacIntosh 8100/80 Power PC and finally on the hard drive. The raw data files were then backed up onto magneto-optical discs and post-processed using a Labview program.

Before storage and processing, data from the individual combustion chamber firings were passed through a Butterworth 4th order digital bandpass filter of 15 kHz–45 kHz range. This is done to isolate frequencies which could only be significantly excited within the combustion chamber by a knocking event. The filtered signal was then "windowed" for 3 milliseconds near top dead center of piston travel (compression/expansion stroke). The filtered, windowed signal was then sent through an absolute-value function and integrated to obtain a pressure-time-intensity expression of the acoustic energy supplied to the filter in the 15 kHz–45 kHz band of frequencies detected by the system. This value was used to create a scale with which knock intensity was measured. If the intensity of the integral was found to be greater than 20 on this scale, it was determined to be a knocking case and the knocking events per 200 cycles were recorded.

In rating the performance of the Avgas based on knocking cycles, an acceptable performance level is fewer than 50 knocking events per 400 cycles.

Figure 3:
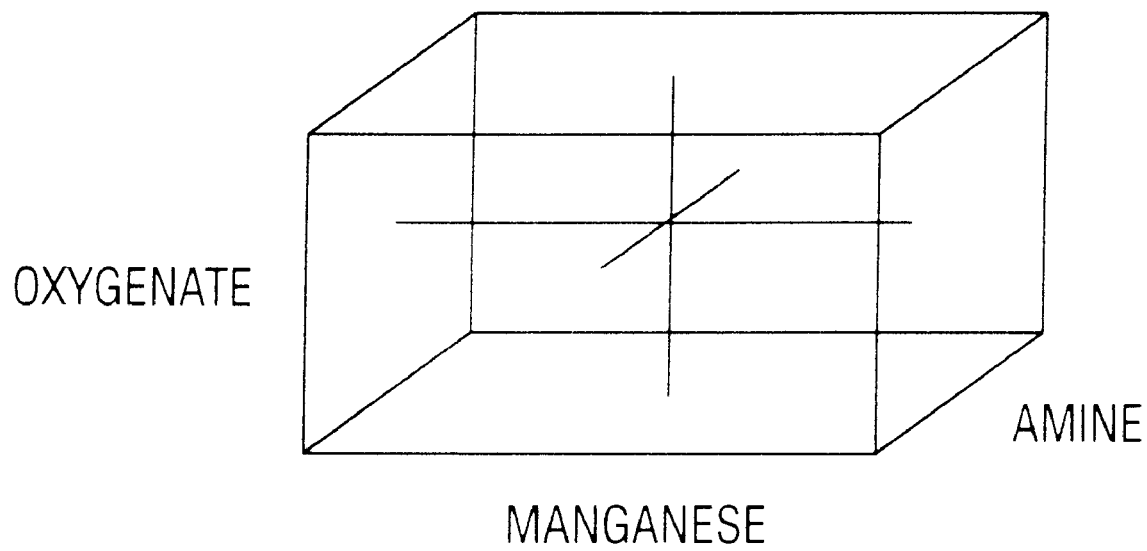
Figure 4:
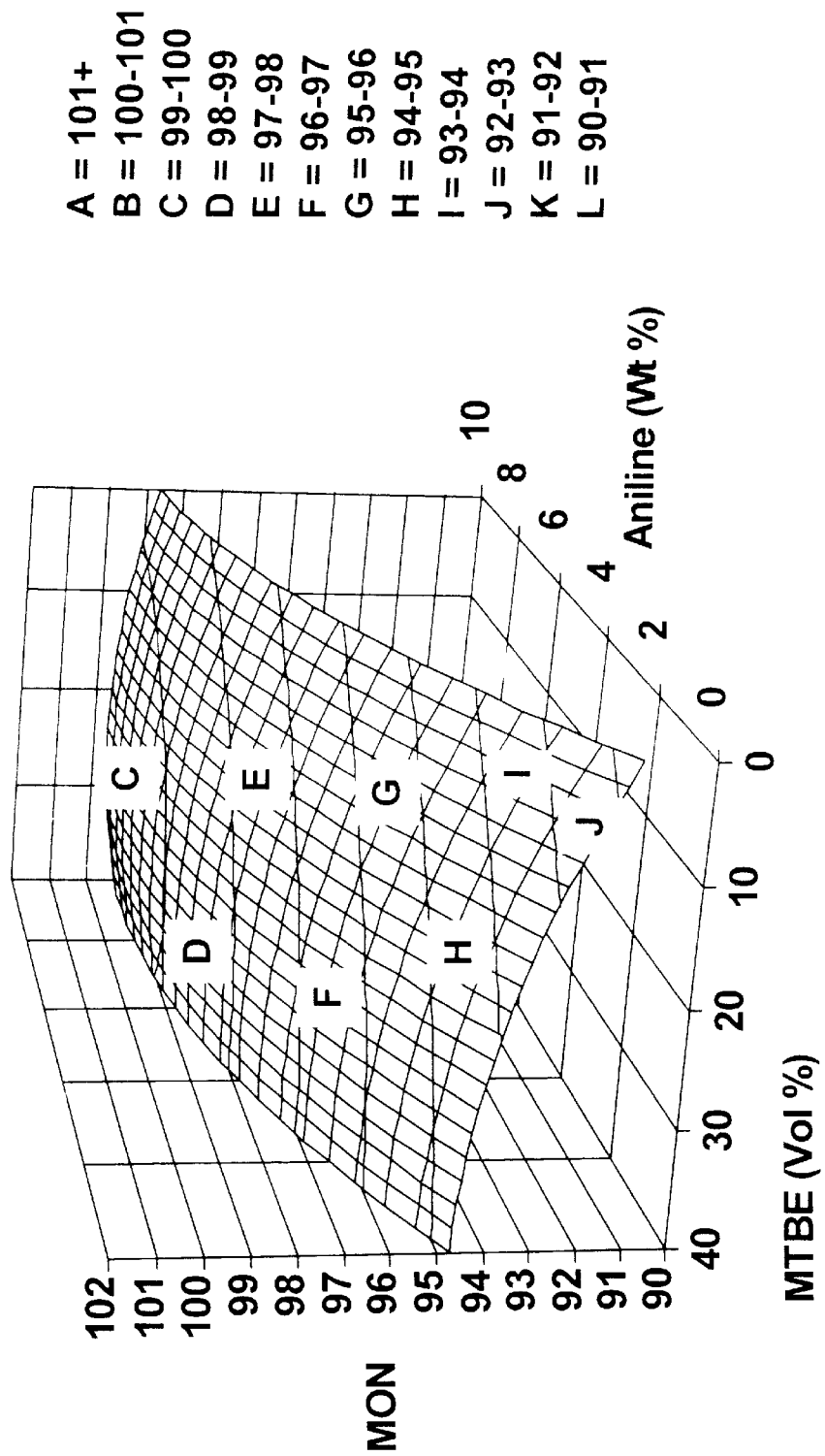
Figure 5:
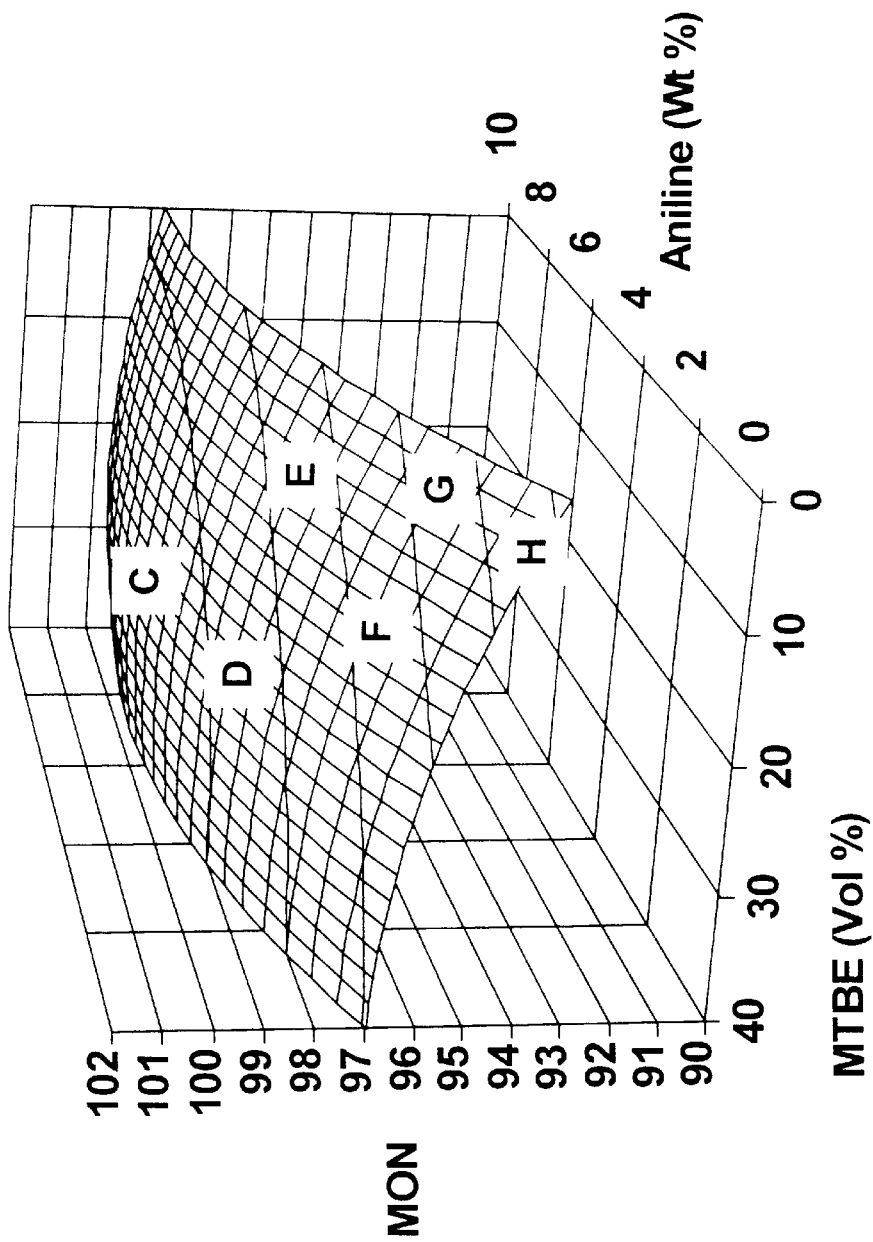
Figure 6:
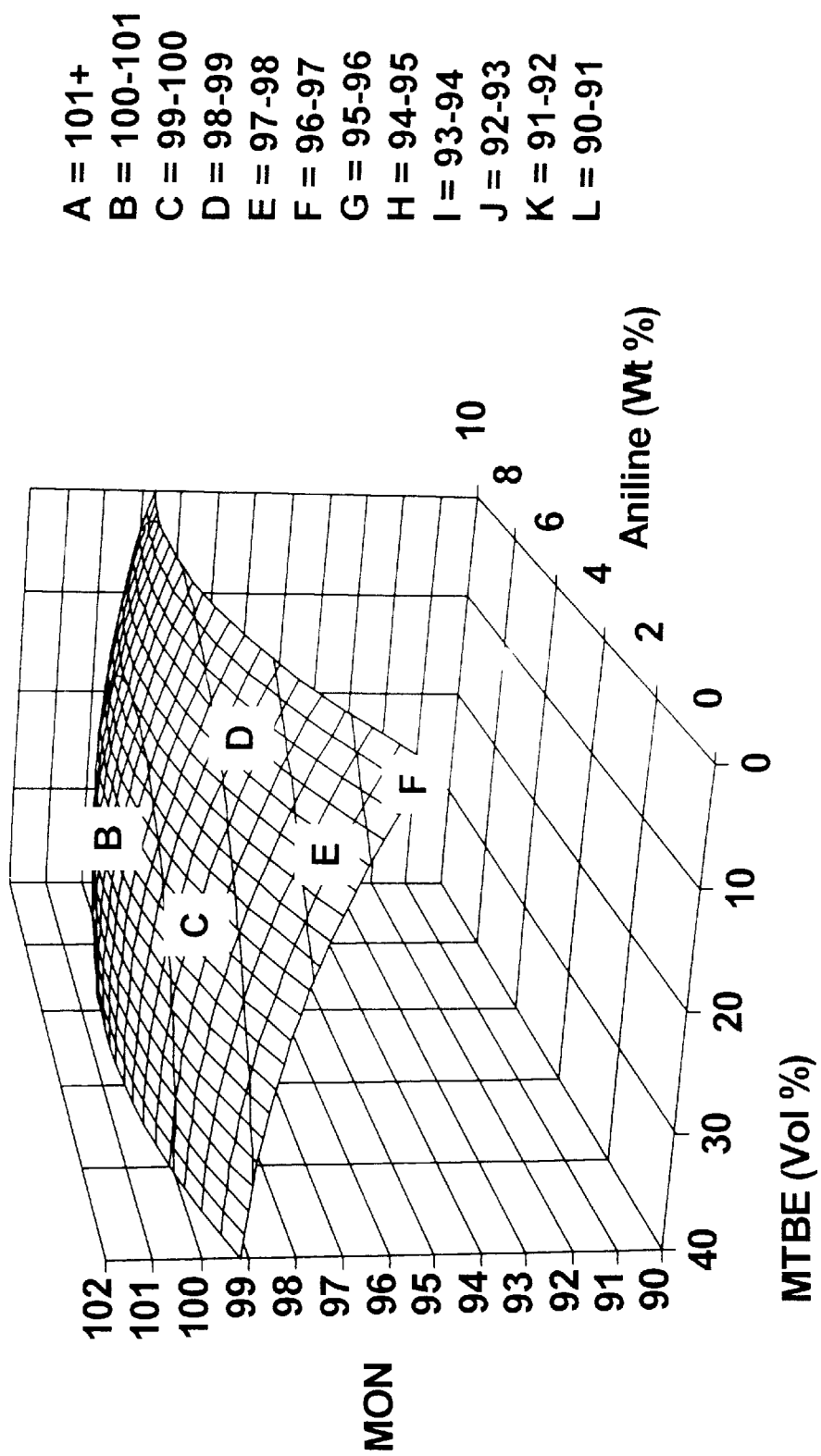
Figure 7:
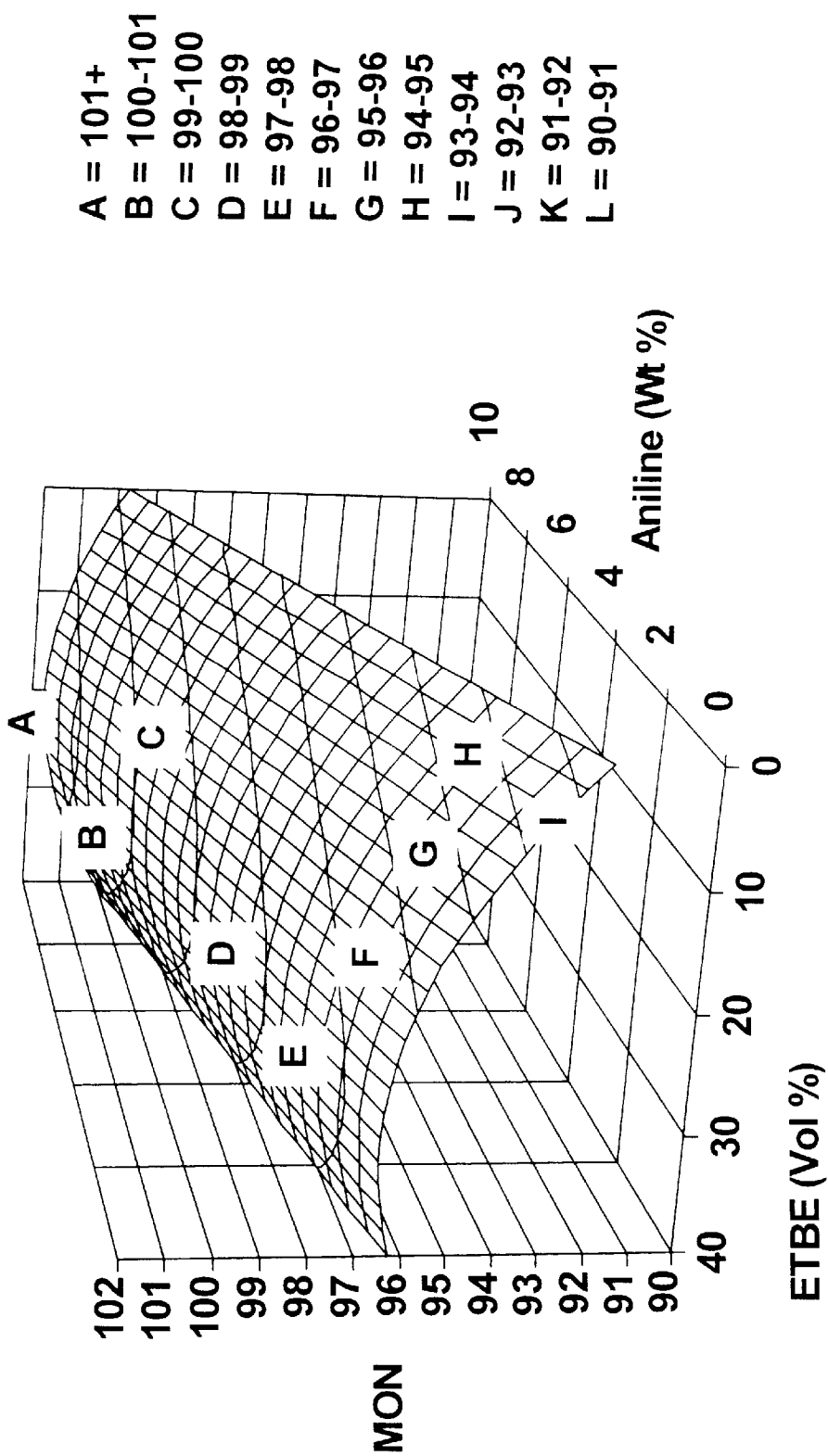
Figure 8:
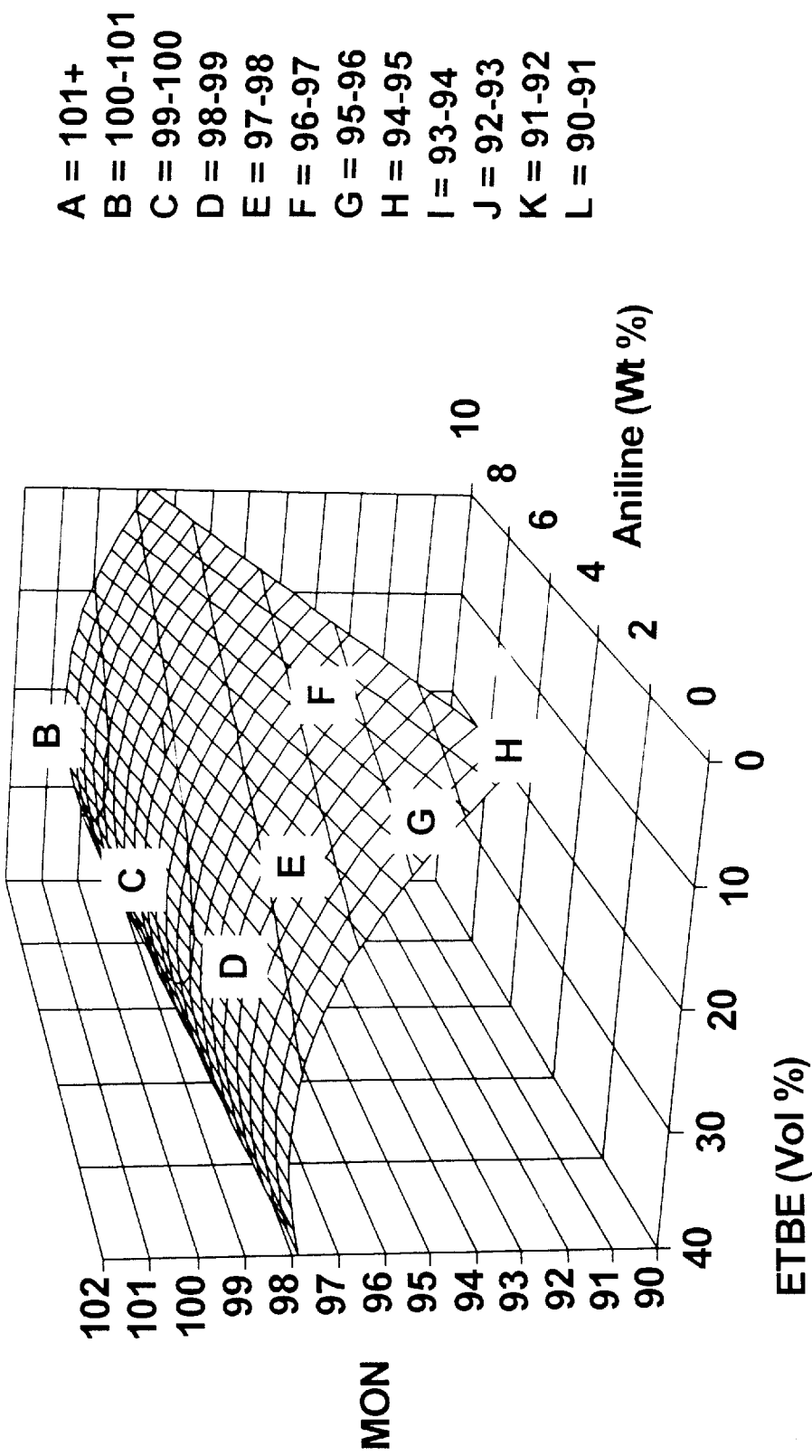
Figure 9:
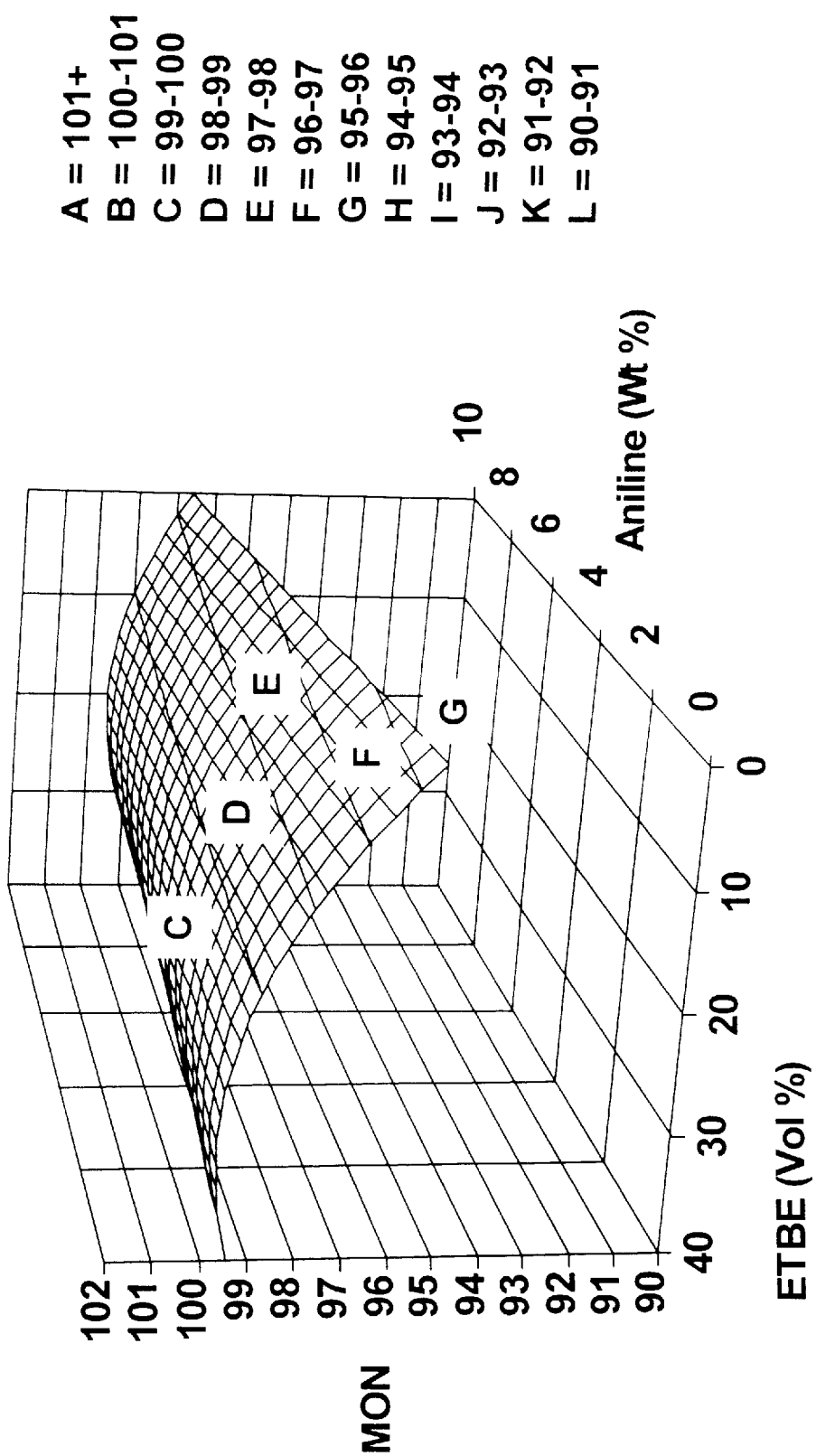
Figure 10:
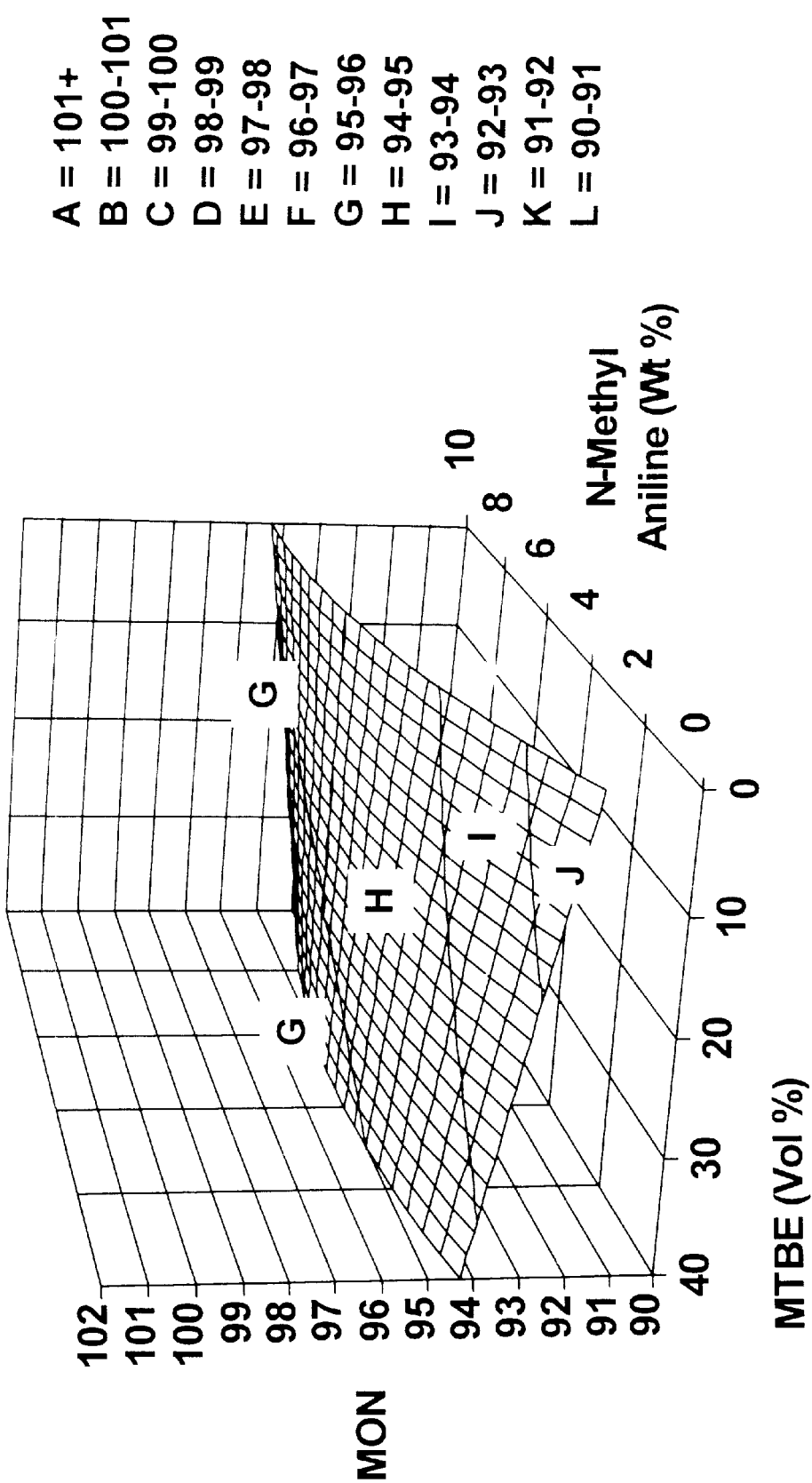
Figure 11:
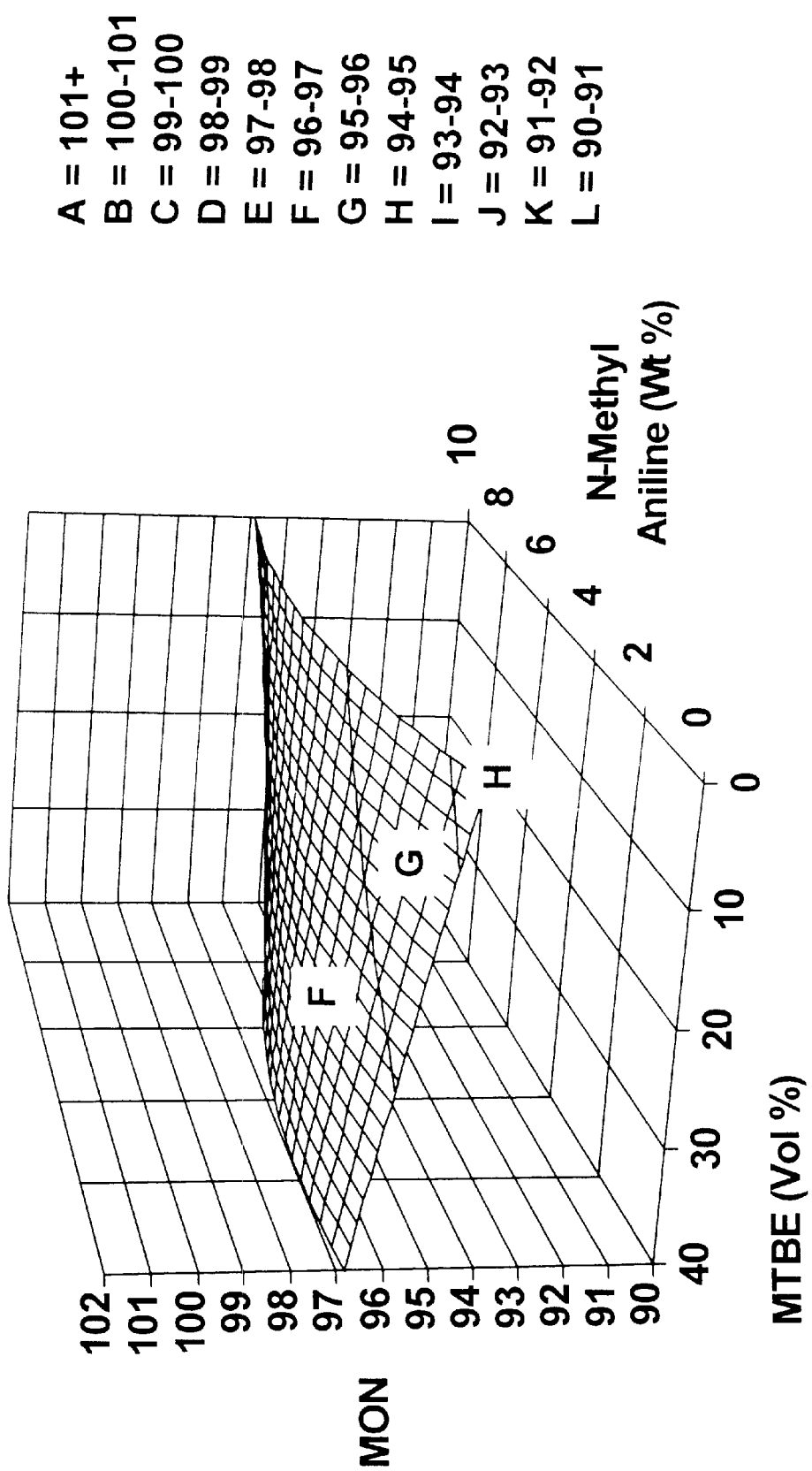
Figure 12:
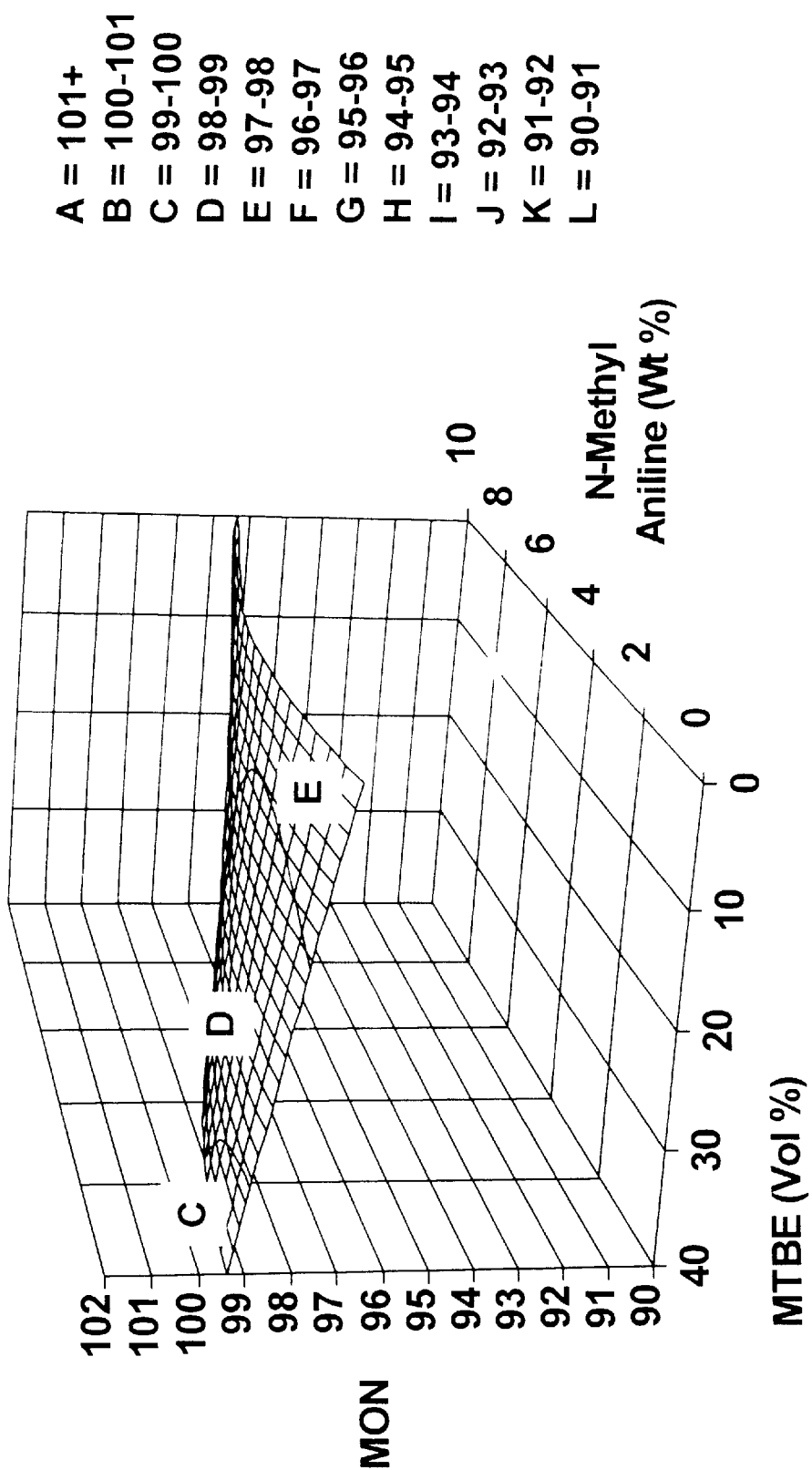
Figure 13:
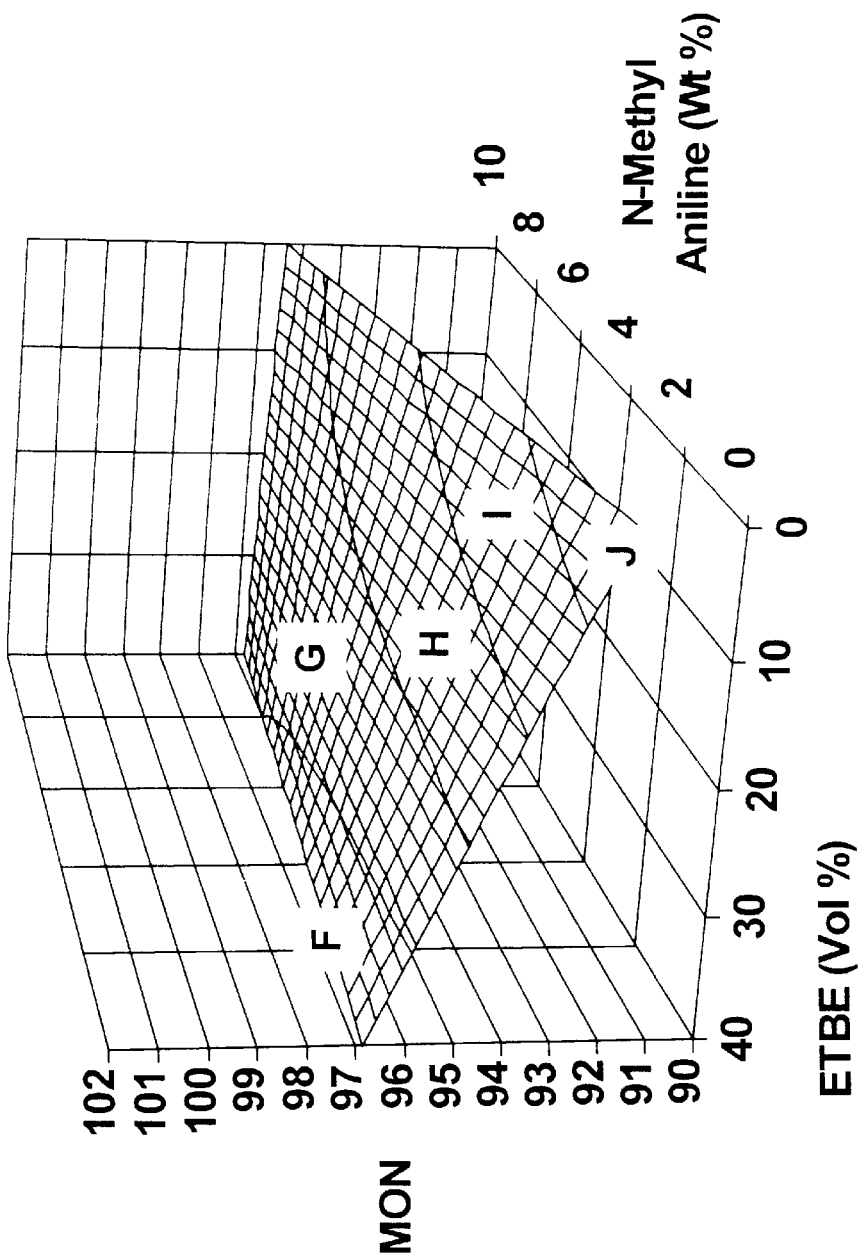
Figure 14:
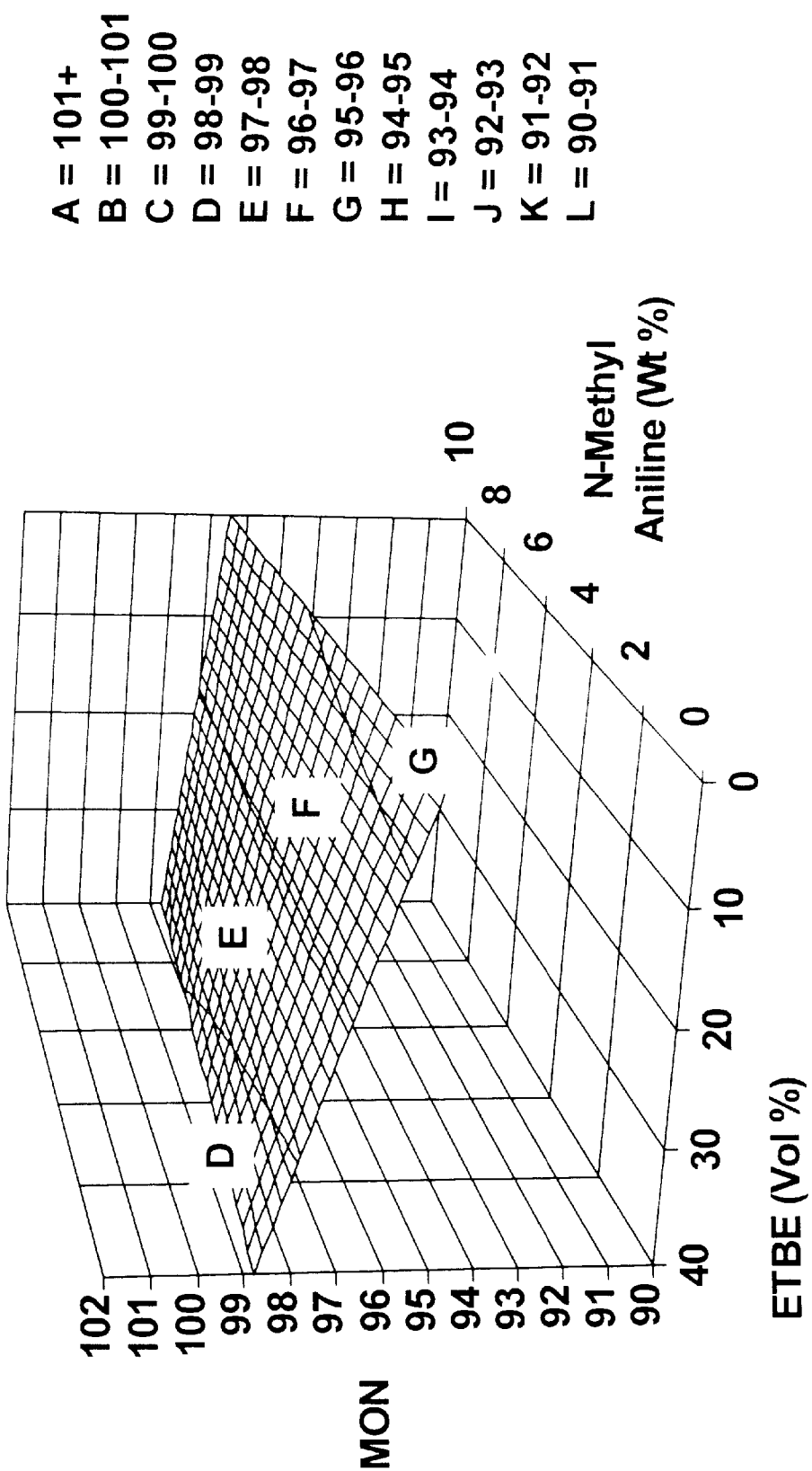
Figure 15:
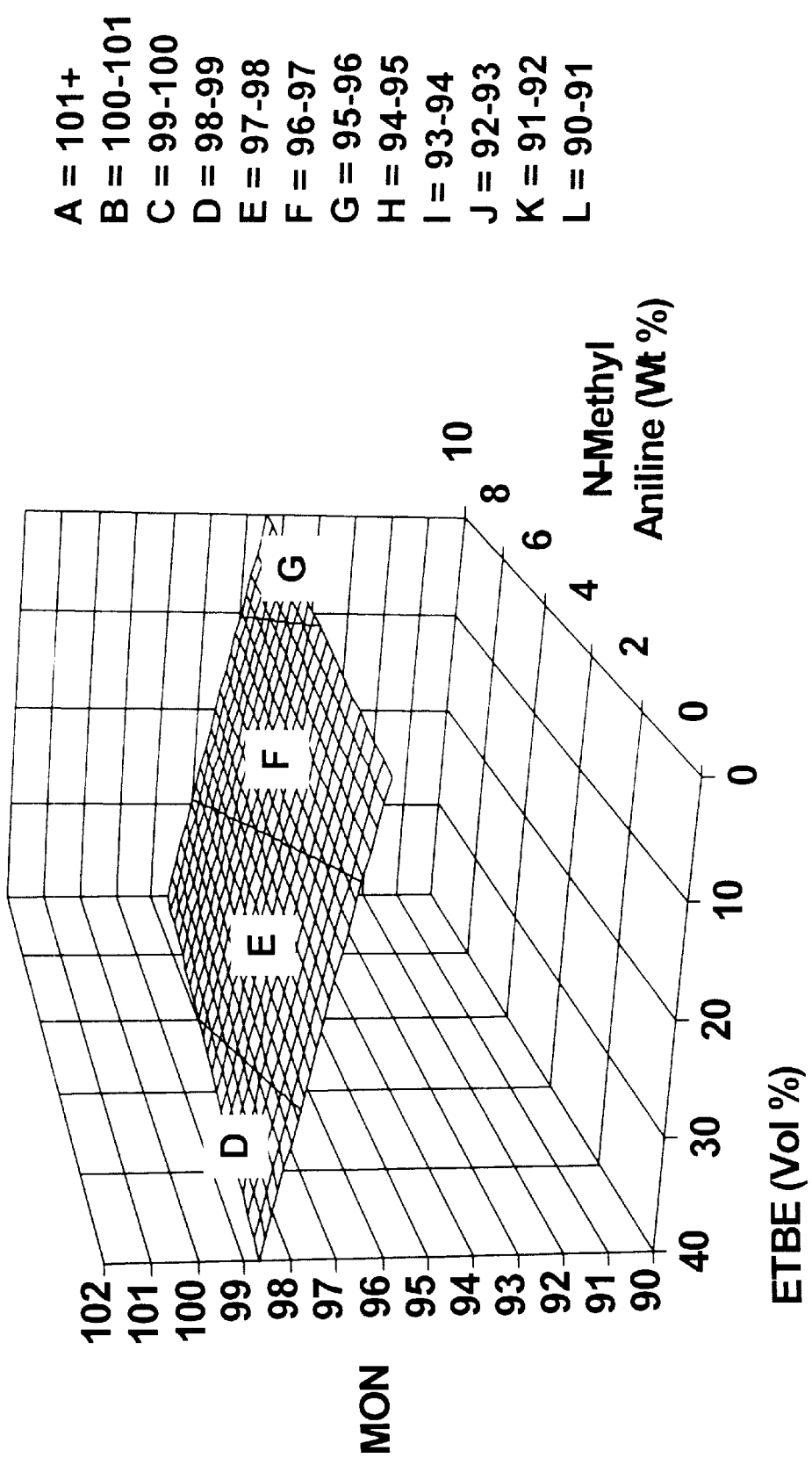
Figure 16:
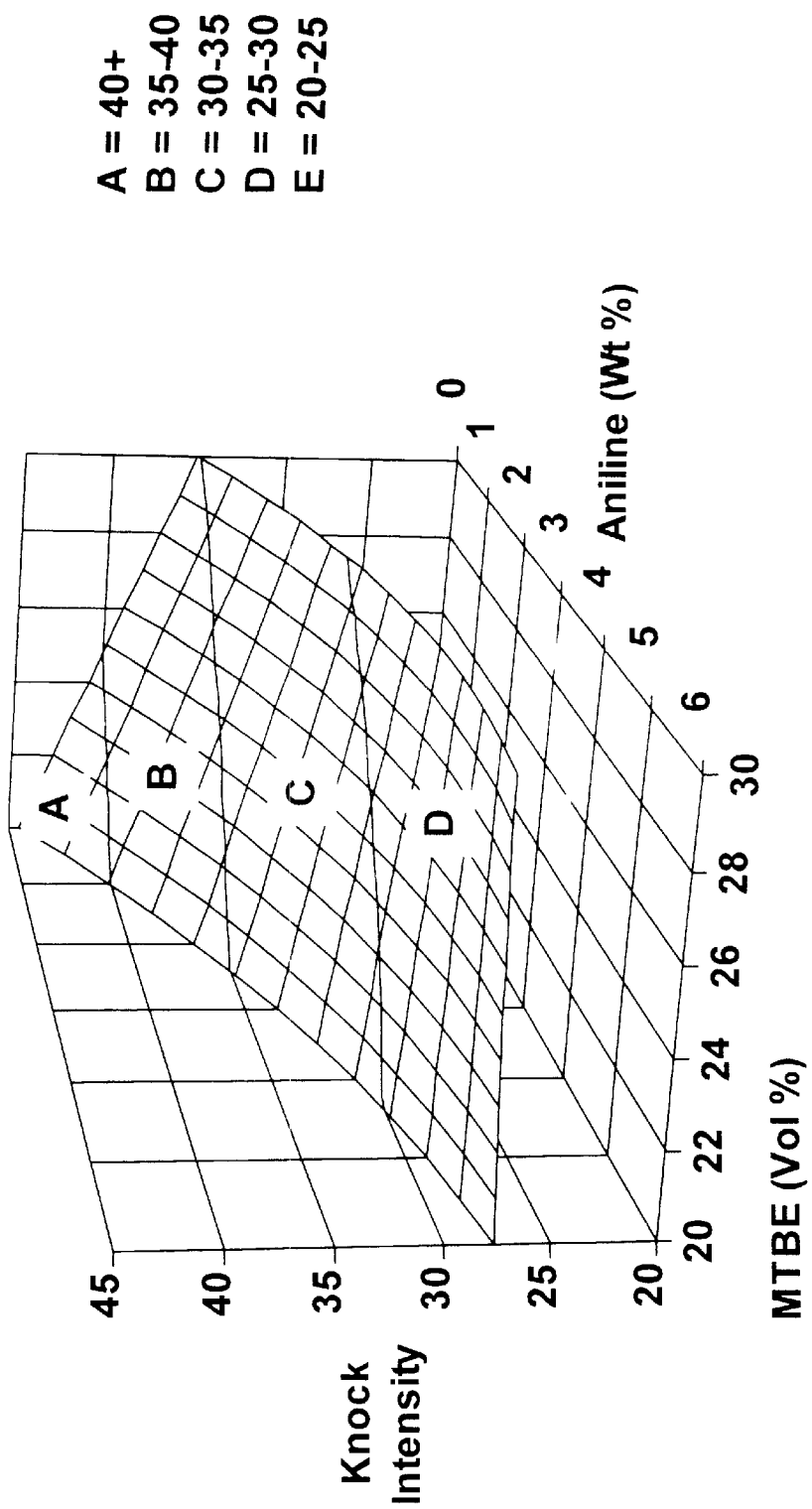
Figure 17:
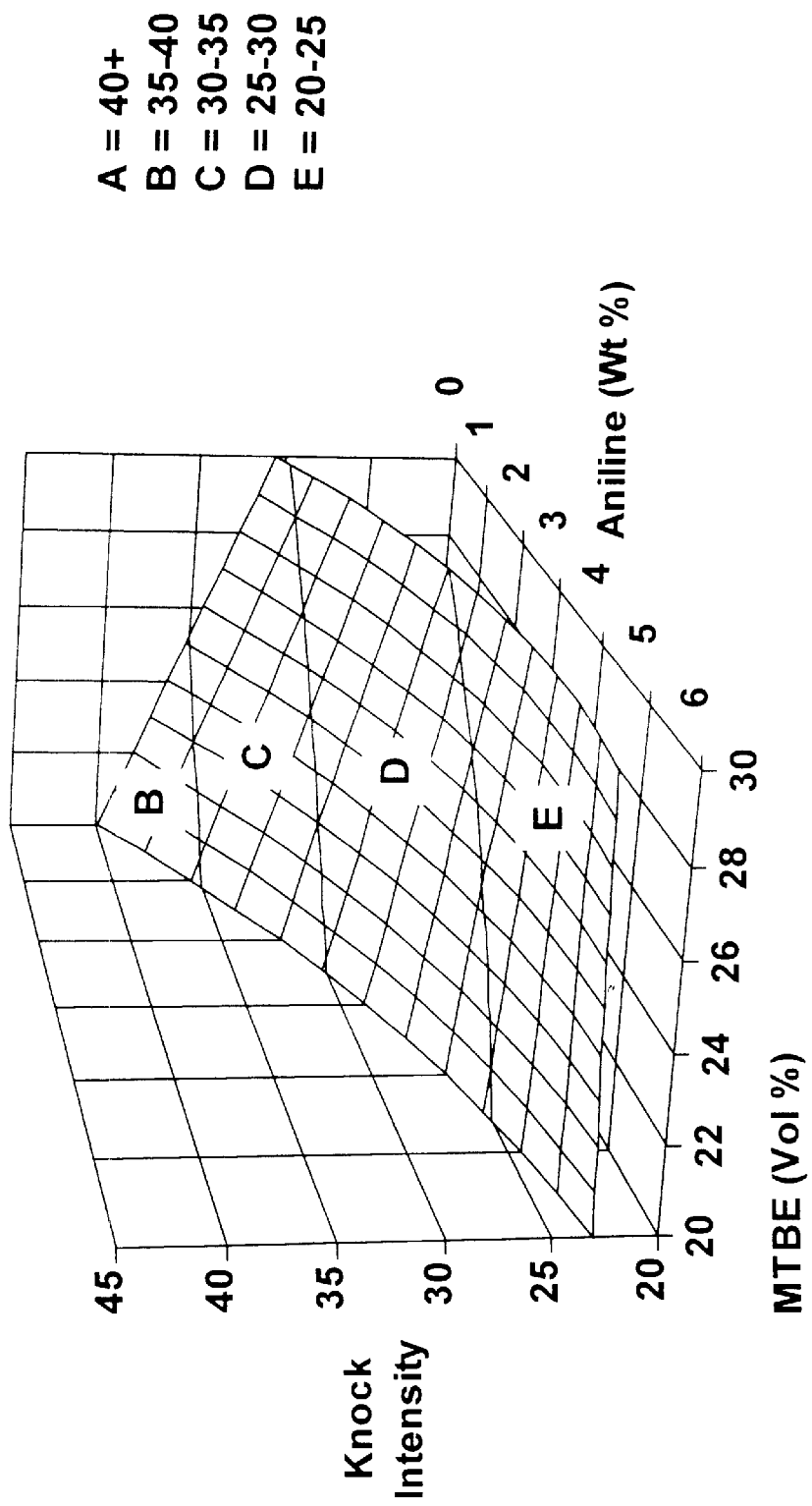
Figure 18:
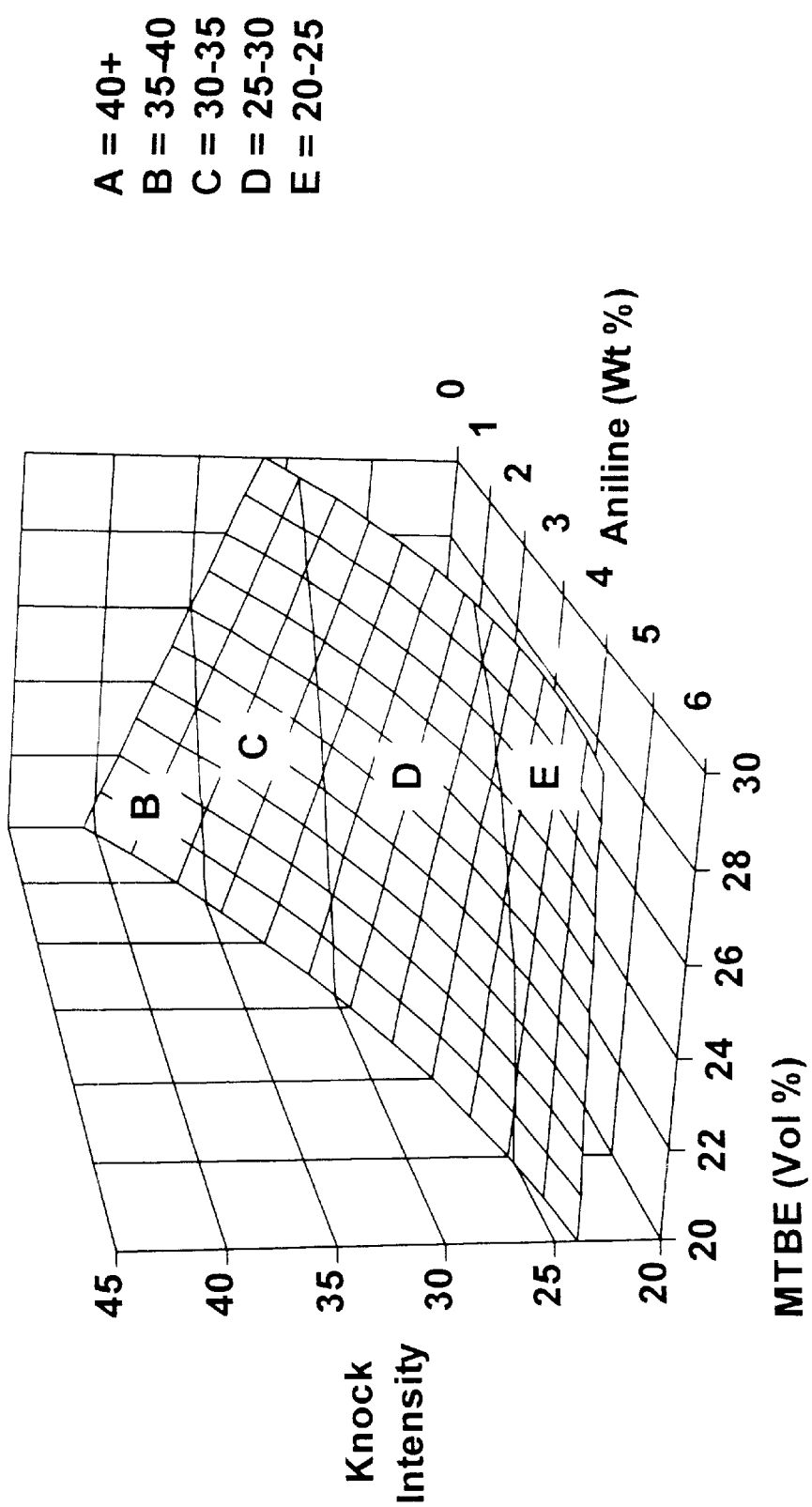
Figure 19:
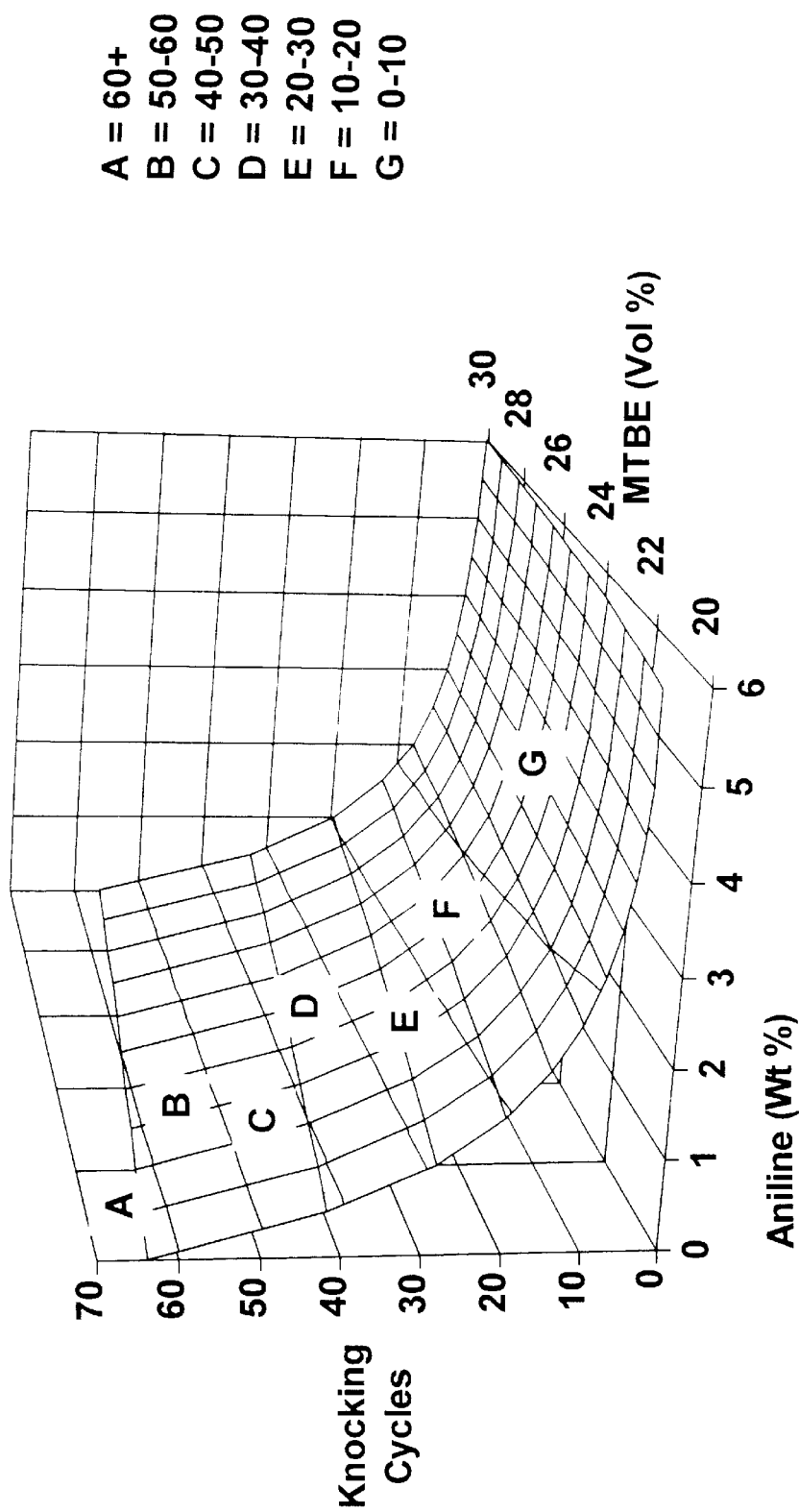
Figure 20:
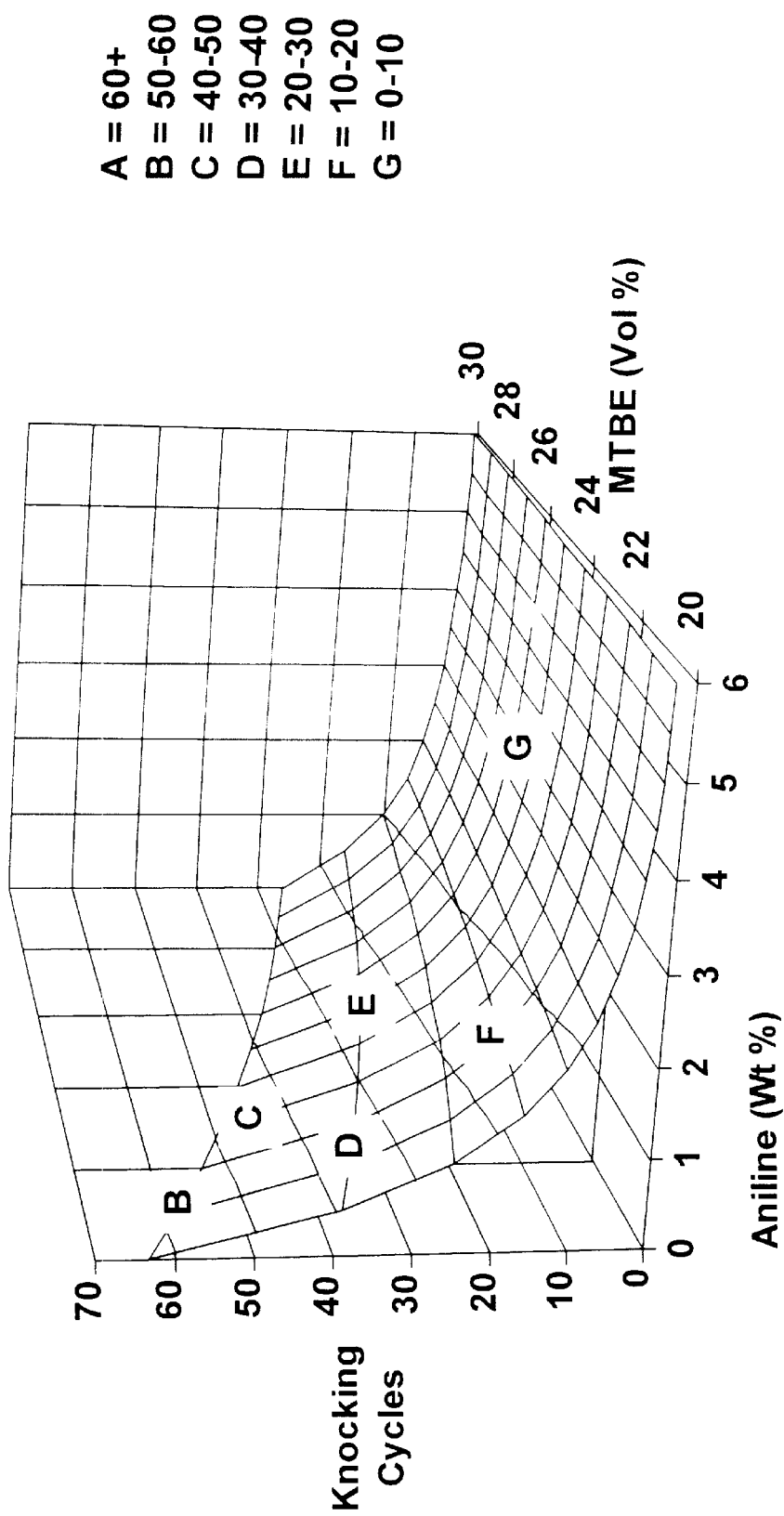
Figure 21:
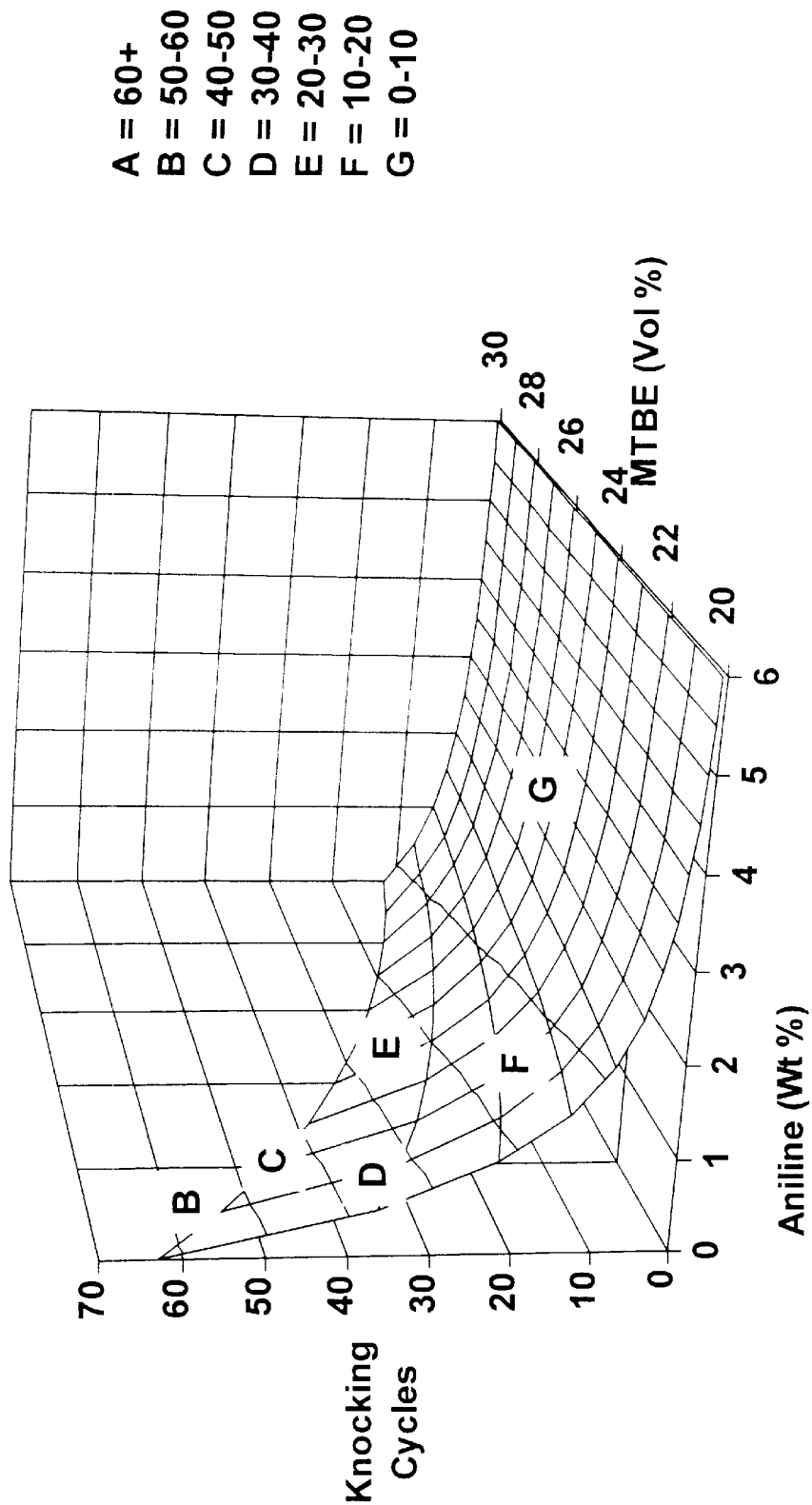
Figure 22:
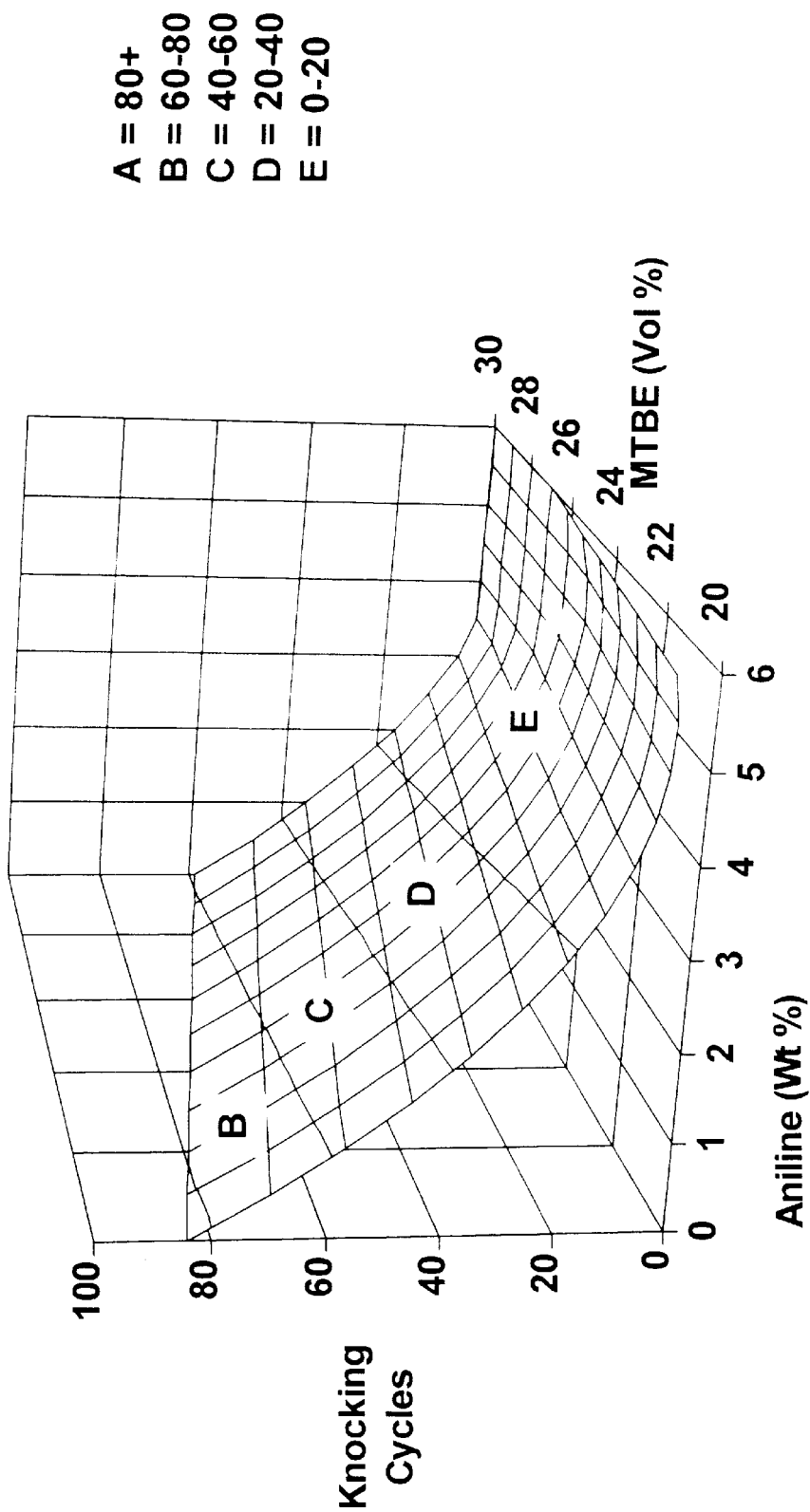
Figure 23:
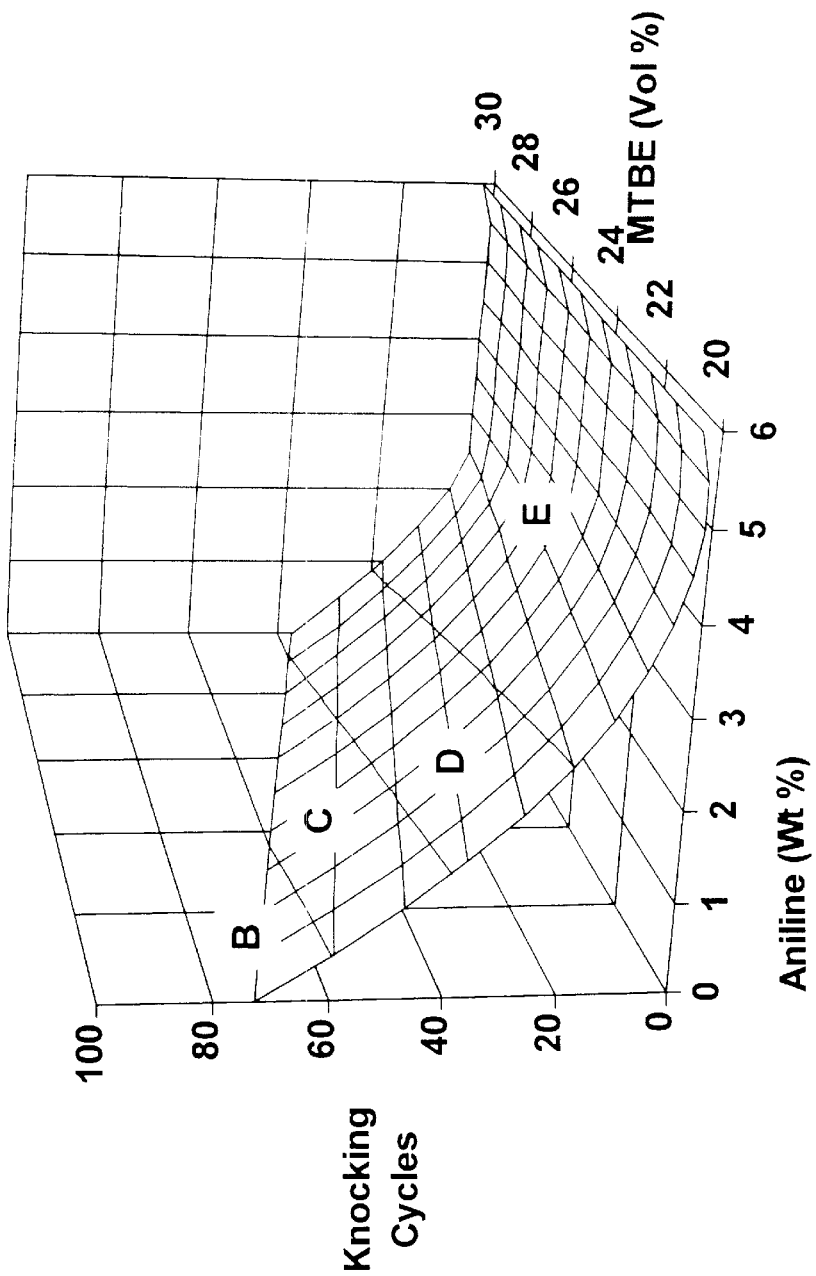
Figure 24:
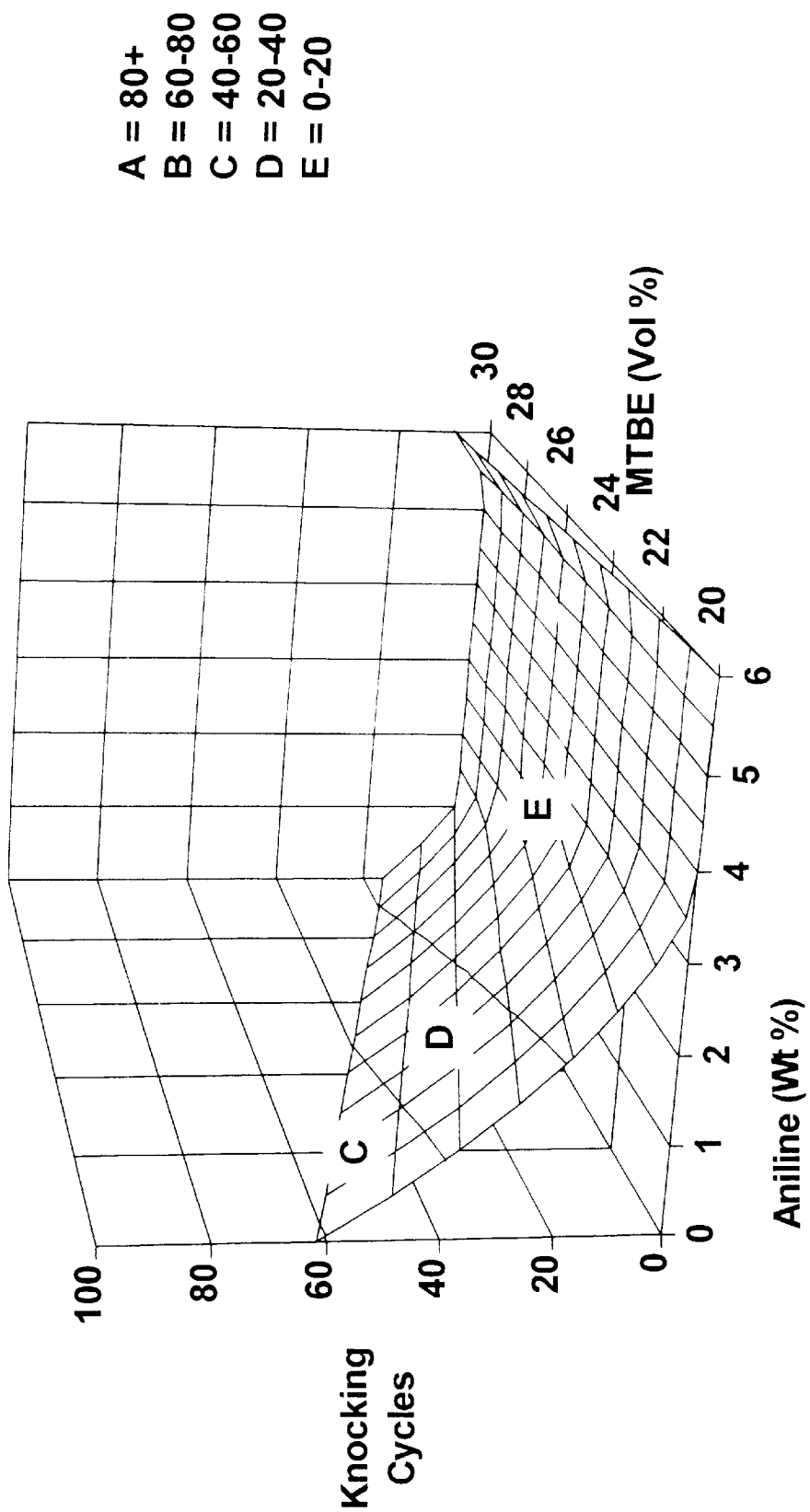
Figure 25:
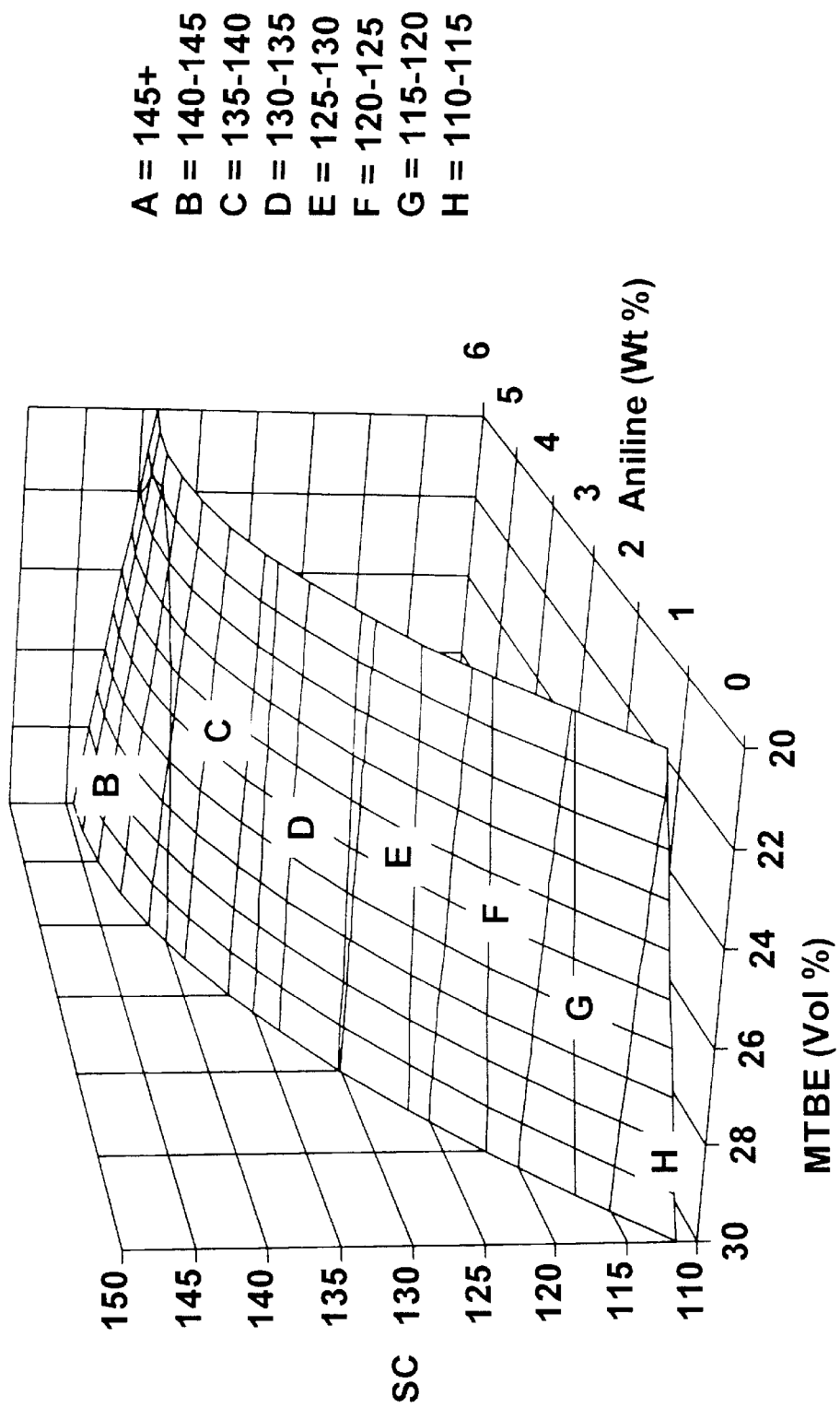
Figure 26:
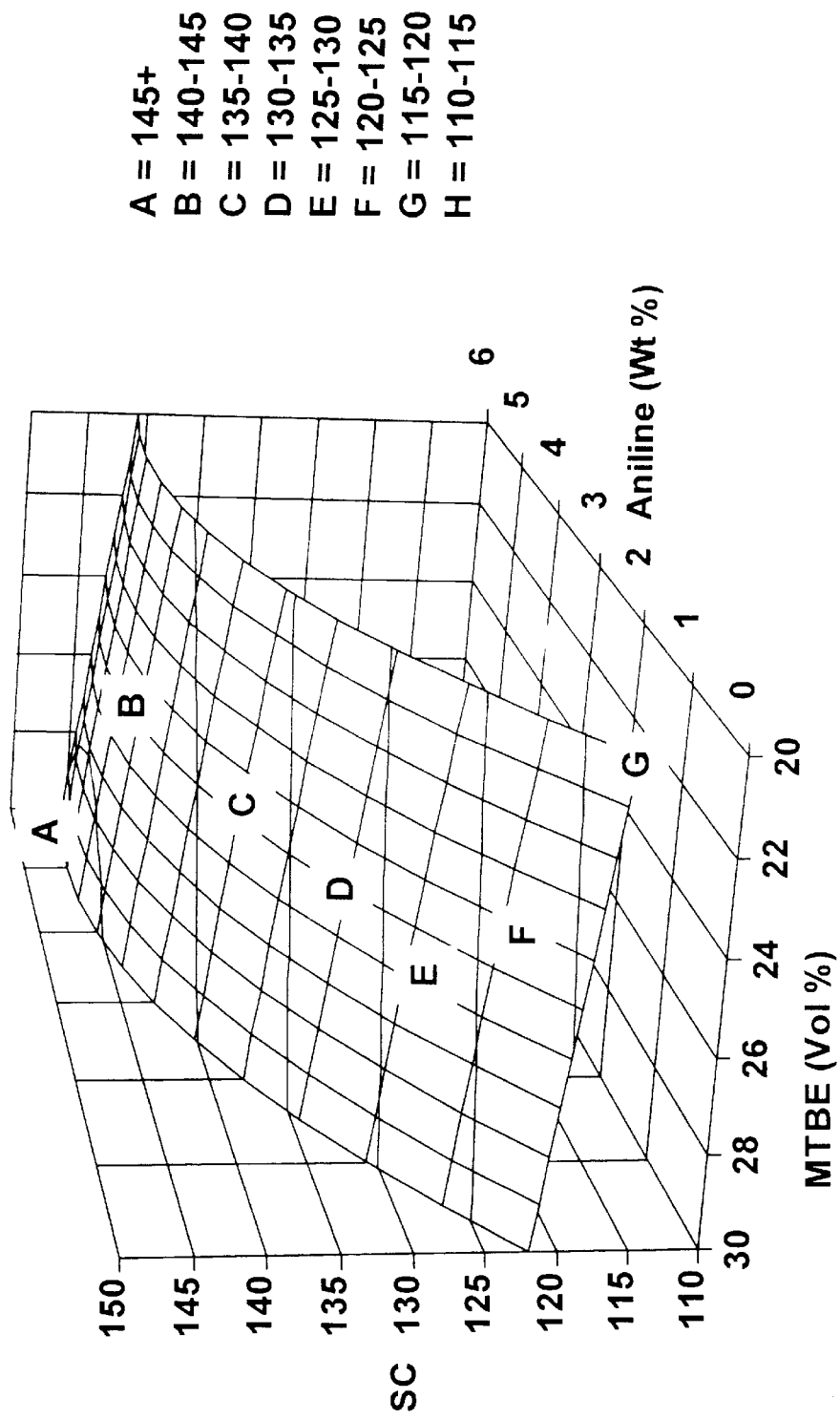
Figure 27:
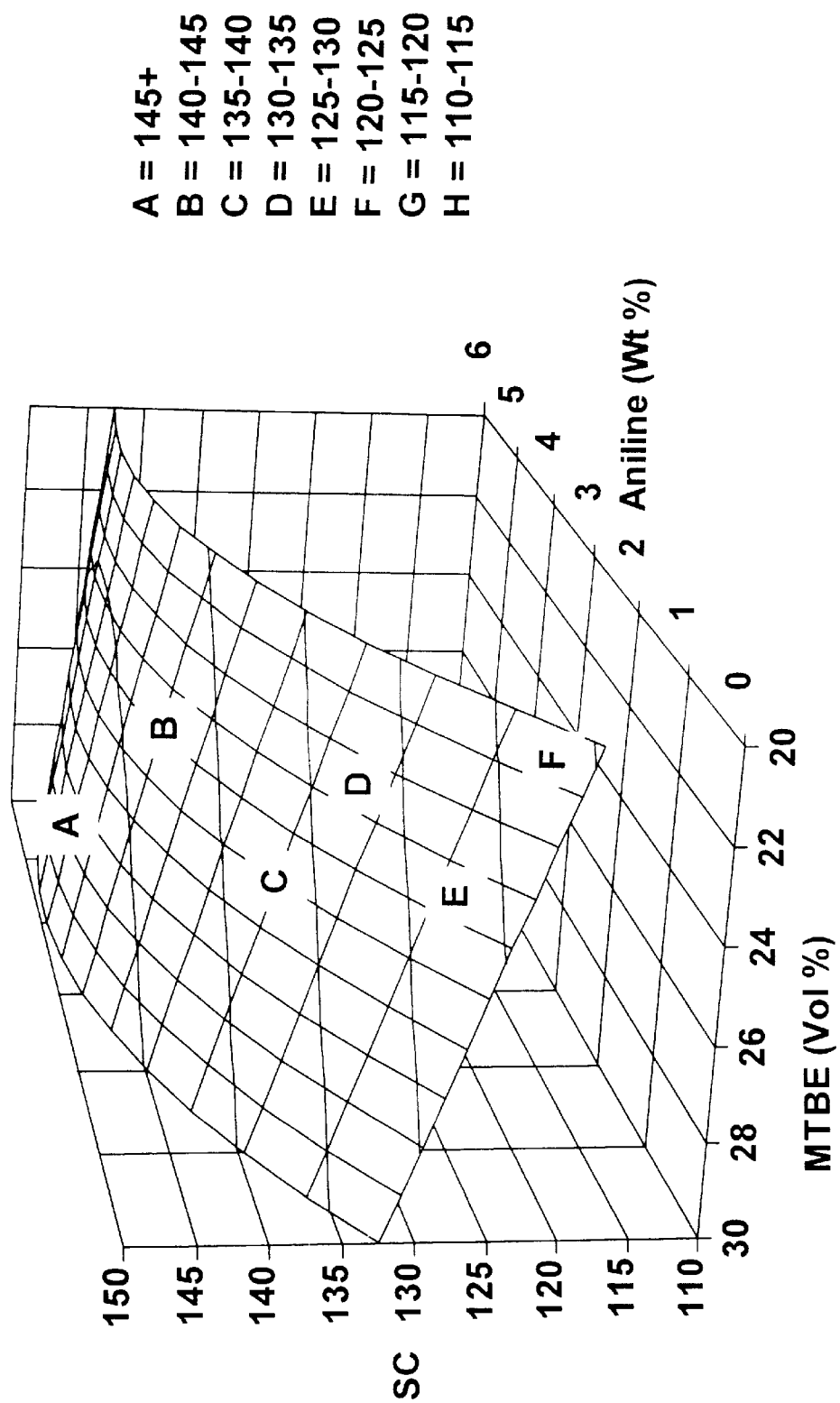
Figure 28:
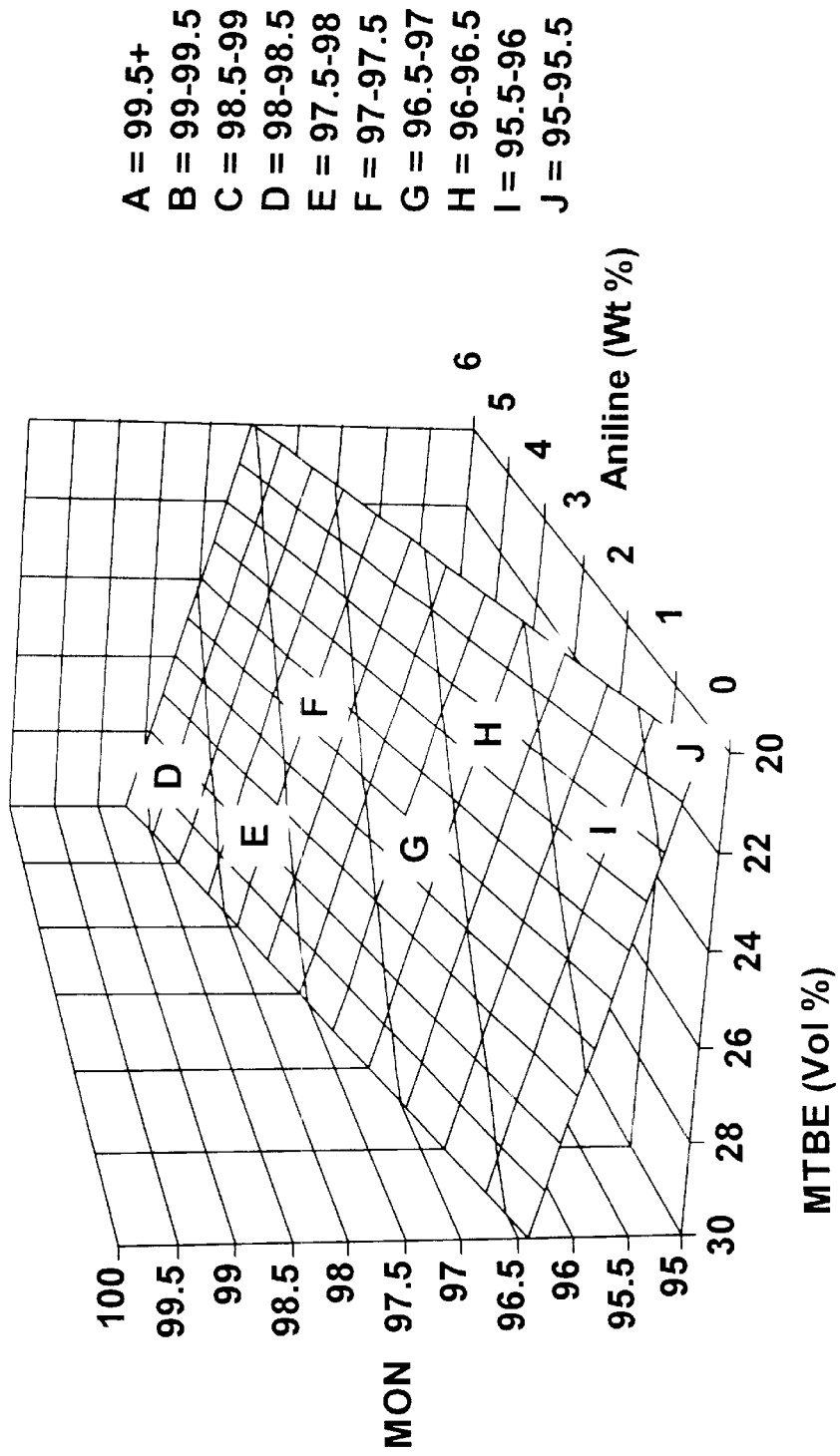
Figure 29:
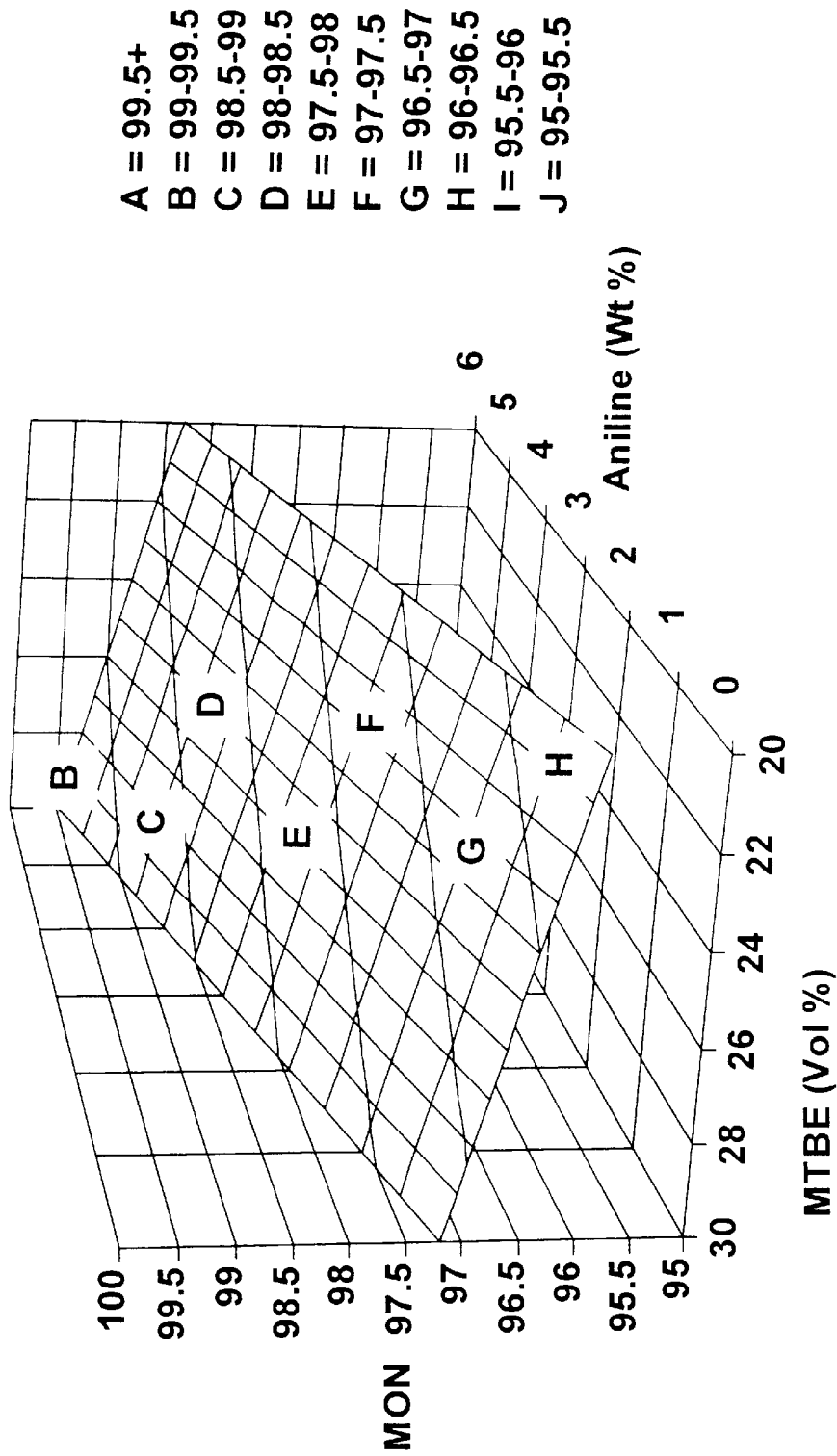
Figure 30:
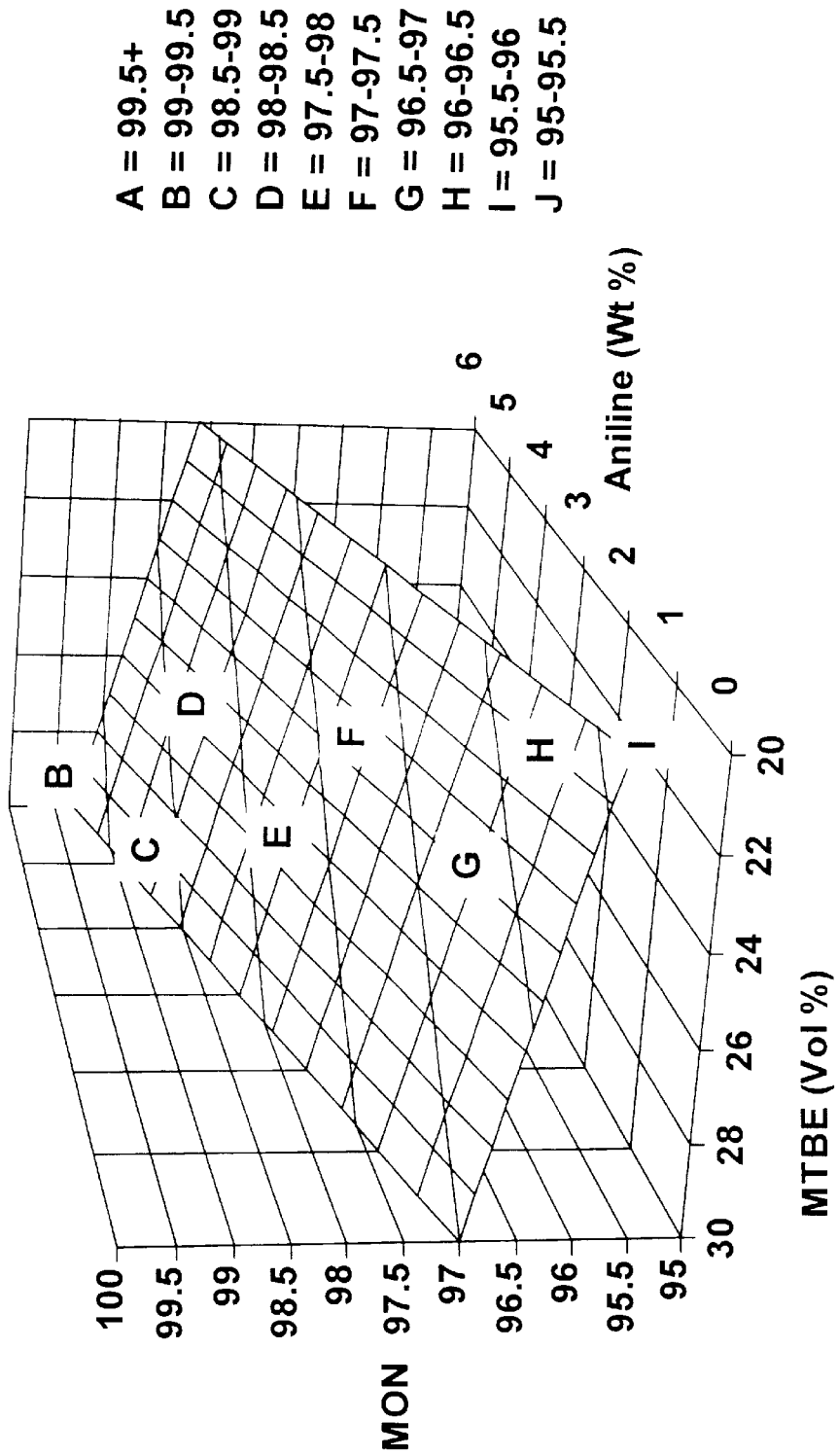

D. Determination of Non-Linear Models for Identifying Aviation Fuel Compositions with Desirable MON Ratings The effects of various fuel formulations on MON ratings were determined using statistically designed experiments. More specifically, the complex relationships between the in-cylinder oxidation chemistries of the octane boosting additives and the basefuel were investigated using face centered cube statistical designs (See, e.g., FIG. 3).

The statistically designed experiments measured the MON values of specific fuel formulations which were combinations of three variables (Manganese level, aromatic amine level and oxygenate level) mixed with a wide boiling range alkylate. The three variables and their respective concentration ranges define the x, y and z axes of the cube. (See FIG. 3). The cube faces (surfaces) and the space within the cube define all the interaction points for investigation. The three variable test ranges were 0–10 wt % aromatic amine, 0–0.5 g/gal manganese (Mn) and 0–40 vol. % oxygenate (an alkyl tertiary butyl ether). The manganese may be provided by a corresponding amount of methyl cyclopentadienyl manganese tricarbonyl (MMT). The two oxygenates tested were methyl tertiary butyl ether (MTBE) and ethyl tertiary butyl ether (ETBE). In total, four test cubes were designed to measure the numerous fuel combinations and therefore potentially different chemical oxidation interactions. The four cube design layouts are listed in Table 4. Aniline and n-methyl aniline were the aromatic amines chosen for complete statistical analyses.

TABLE 4

Design for Testing Cube Independent Variables

| Cube Number | Basefuel | Variable 1 | Variable 2 | Variable 3 |
|---|---|---|---|---|
| 1 | Wide boiling range | MMT | MTBE | Aniline |
| 2 | Wide boiling range | MMT | ETBE | Aniline |
| 3 | Wide boiling range | MMT | MTBE | n-Methyl Aniline |
| 4 | Wide boiling range | MMT | ETBE | n-Methyl Aniline |

The MON values were measured at specific points along the three cube axes as well as the cube center point. Multiple measurements were made at the center point to calculate the MON variation level with the assumption being it is constant over all the test space of the design, i.e. essentially a ten MON number range, 91–101. Polynomial curves were fitted to the data to define equations which describe the three variable interactions with respect to MON over the entire cube test space. From these equations, the MON performance for all variable combinations can be predicted within the test space defined by the maximum and minimum concentration ranges of the variables. Some of the predicted and measured MON values have been summarized in Tables 5–8. The remainder of the predicted values can be derived from the prediction equations.

TABLE 5

Predicted (p) MON versus Measured (m) MON for Oxygenate + Aniline Manganese = 0 g/gal

| | Aniline | | | | | | | |
|---|---|---|---|---|---|---|---|---|
| | 0 wt % | | 2 wt % | | 6 wt % | | 10 wt % | |
| Vol. % | MON (p) | MON (m) | MON (p) | MON (m) | MON (p) | MON (m) | MON (p) | MON (m) |
| MTBE | | | | | | | | |
| 0 | 91.5 | 91.1 | 93.8 | 94.6 | 97.1 | | 98.6 | 98.8 |
| 10 | 92.8 | | 95.0 | | 98.0 | | 99.3 | |
| 20 | 93.8 | 93.6 | 95.8 | | 98.6 | 98.9 | 99.6 | |
| 30 | 94.4 | | 96.3 | | 98.8 | | 99.6 | |
| 40 | 94.7 | 95.2 | 96.5 | 97.0 | 98.7 | | 99.2 | 99.0 |
| ETBE | | | | | | | | |
| 0 | 92.3 | 91.1 | 93.8 | 95.9 | 96.8 | | 99.7 | 97.6 |
| 10 | 94.6 | | 95.9 | | 98.5 | | 101.1 | |
| 20 | 96.0 | 94.0 | 97.2 | | 99.4 | 98.8 | 101.7 | |
| 30 | 96.6 | | 97.5 | | 99.4 | | 161.3 | |
| 40 | 96.3 | 96.2 | 97.0 | 97.2 | 98.6 | | 100.1 | 101.1 |

TABLE 6

Predicted MON versus Measured MON for Oxygenate + Aniline Manganese = 0.5 g/gal

| | Aniline | | | | | | | |
|---|---|---|---|---|---|---|---|---|
| | 0 wt % | | 2 wt % | | 6 wt % | | 10 wt % | |
| Vol. % | MON (p) | MON (m) | MON (p) | MON (m) | MON (p) | MON (m) | MON (p) | MON (m) |
| MTBE | | | | | | | | |
| 0 | 96.0 | 95.3 | 97.4 | 97.7 | 98.9 | | 98.7 | 99.1 |
| 10 | 97.3 | | 98.5 | | 99.8 | | 99.4 | |
| 20 | 98.2 | 99.1 | 99.4 | | 100.4 | 99.6 | 99.7 | |
| 30 | 98.9 | | 99.9 | | 100.6 | | 99.7 | |
| 40 | 99.2 | 100.3 | 100.1 | 99.6 | 100.6 | | 99.3 | 99.8 |
| ETBE | | | | | | | | |
| 0 | 95.5 | 95.5 | 95.9 | 96.0 | 96.8 | | 97.6 | 97.8 |
| 10 | 97.8 | | 98.0 | | 98.5 | | 99.0 | |
| 20 | 99.2 | 97.5 | 99.3 | | 99.4 | 100.5 | 99.5 | |
| 30 | 99.8 | | 99.6 | | 99.4 | | 99.2 | |
| 40 | 99.4 | 98.4 | 99.1 | 100.9 | 98.6 | | 98.0 | 97.1 |

TABLE 7

Predicted (p) MON versus measured (m) MON for Oxygenate + n-Methyl Aniline  
Manganese = 0.0 g/gal

|  | n-Methyl Aniline | | | | | | | |
|---|---|---|---|---|---|---|---|---|
|  | 0 wt % | | 2 wt % | | 6 wt % | | 10 wt % | |
| Vol. % | MON (p) | MON (m) | MON (p) | MON (m) | MON (p) | MON (m) | MON (p) | MON (m) |
| MTBE | | | | | | | | |
| 0 | 92.1 | 91.1 | 93.4 | 94.0 | 95.0 | | 95.4 | 94.7 |
| 10 | 92.6 | | 93.7 | | 95.0 | | 95.0 | |
| 20 | 93.2 | 93.6 | 94.1 | | 95.0 | 94.9 | 94.6 | |
| 30 | 93.7 | | 94.5 | | 95.0 | | 94.2 | |
| 40 | 94.3 | 95.2 | 94.8 | 94.8 | 95.0 | | 93.9 | 94.6 |
| ETBE | | | | | | | | |
| 0 | 92.1 | 91.1 | 92.8 | 93.8 | 94.1 | | 95.4 | 95.6 |
| 10 | 93.3 | | 93.8 | | 94.6 | | 95.5 | |
| 20 | 94.5 | 94.0 | 94.7 | | 95.2 | 95.9 | 95.6 | |
| 30 | 95.7 | | 95.7 | | 95.7 | | 95.7 | |
| 40 | 96.9 | 96.2 | 96.6 | 96.2 | 96.2 | | 95.8 | 96.5 |

TABLE 8

Predicted (p) MON versus measured (m) MON for Oxygenate + n-Methyl Aniline,  
Manganese = 0.5 g/gal

|  | n-Methyl Aniline | | | | | | | |
|---|---|---|---|---|---|---|---|---|
|  | 0 wt % | | 2 wt % | | 6 wt % | | 10 wt % | |
| Vol. % | MON (p) | MON (m) | MON (p) | MON (m) | MON (p) | MON (m) | MON (p) | MON (m) |
| MTBE | | | | | | | | |
| 0 | 97.2 | | 97.7 | 99.4 | 97.7 | | 96.4 | 95.9 |
| 10 | 97.7 | | 98.0 | | 97.7 | | 96.0 | |
| 20 | 98.3 | | 98.4 | | 97.7 | 97.5 | 95.6 | |
| 30 | 98.8 | | 98.8 | | 97.7 | | 95.3 | |
| 40 | 99.4 | | 99.1 | 98.7 | 97.7 | | 94.9 | 95.3 |
| ETBE | | | | | | | | |
| 0 | 96.6 | | 96.3 | 97.4 | 95.9 | | 95.5 | 95.9 |
| 10 | 97.1 | | 96.9 | | 96.4 | | 96.0 | |
| 20 | 97.6 | | 97.4 | | 96.9 | 97.2 | 96.5 | |
| 30 | 98.2 | | 97.9 | | 97.5 | | 97.0 | |
| 40 | 98.7 | | 98.5 | 97.3 | 98.0 | | 97.5 | 98.4 |

The equations which describe the three variable (oxygenate, Manganese and aromatic amine) interactions and ultimately predict MON levels are listed in Table 8A.

TABLE 8A

MON Prediction Equations

Test Cube: MTBE/Aniline/Manganese

MON = 91.54 + (0.1466 * MTBE) + (8.827 * Mn) + (1.252 * Aniline) − (0.006492 * MTBE * Aniline) − (0.8673 * Mn * Aniline) − (0.001667 * MTBE$^2$) − (0.05437 * Aniline$^2$)

Test Cube: MTBE/n-Methyl Aniline/Manganese

MON = 92.06 + (0.05563 * MTBE) + (10.23 * Mn) + (0.7308 * nMA) − (0.009273 * MTBE * nMA) − (0.8220 * Mn * nMA) − (0.04005 * nMA$^2$)

TABLE 8A-continued

MON Prediction Equations

Test Cube: ETBE/Aniline/Manganese

MON = 92.32 + (0.2730 * ETBE) + (6.349 * Mn) + (0.7429 * Aniline) − (0.009016 * ETBE × Aniline) − (1.058 * Mn * Aniline) − (0.004362 * ETBE$^2$)

Test Cube: ETBE/n-Methyl Aniline/Manganese

MON = 92.12 + (0.1185 * ETBE) + (17.04 * Mn) + (0.3317 * nMA) − (0.1306 * ETBE * Mn) − (0.01099 * ETBE * nMA) − (0.8828 * Mn * nMA) + (0.0218 × ETBE * Mn * nMA) − (16.36 * Mn$^2$)

The predicted MON variability for all four design cubes is a combination of engine measurement, fuel blending and equation fitting variability. Table 9 shows the MON engine measurement variability in terms of standard deviations for the four test cubes.

TABLE 9

Standard Deviations for Four Test Cubes

| MTBE, Aniline, Mn | 0.70 MON | ETBE, Aniline, Mn | 0.28 MON |
| MTBE, n-Methyl Aniline, Mn | 0.60 MON | ETBE, n-Methyl Aniline, Mn | 0.55 MON |

The pooled standard deviations for the four test cubes is 0.614 with 18 degrees of freedom. At the 95% confidence limit this results in a variability of 1.83 MON. Variability, as used here, is defined as it is in ASTM MON rating method D-2700—for two single MON measurements, the maximum difference two numbers can have and still be considered equal. However, variability as used here is neither purely repeatability nor reproducibility, but is somewhere between the two definitions. All 168 test fuels were blended from the same chemical/refinery stocks and randomly MON rated by two operators on two MON rating engines over an 8 week period. The accuracy and variability for the equation fitting process of the MON data is shown in Table 10.

TABLE 10

Equation Fitting Variability

| Test Cube | $R^2$ Value | Root Mean Squared Error | Average Error |
|---|---|---|---|
| MTBE + Aniline | 91.0 | 0.82 | 0.54 |
| ETBE + Aniline | 74.5 | 1.29 | 0.85 |
| MTBE + n-Methyl Aniline | 77.3 | 0.99 | 0.70 |
| ETBE + n-Methyl Aniline | 81.3 | 0.81 | 0.61 |

The $R^2$ Values are the proportion of variability in the MON that is explained by the model over the ten octane number range tested. The fuel blending variability was not quantified but is not expected to be a major contributor to the overall predicted MON variability.

The majority of MON results were obtained while the aromatic amines were set in the statistical cube design as aniline and n-methyl aniline. Subsequent work was done to determine other potentially high octane aromatic amines. (See Tables 11–13.) Specific aromatic amines were substituted into two different blends; 1) 80 vol. % wide boiling range alkylate+20 vol. % MTBE and 2) 80 vol. % wide boiling range alkylate+20 vol. % ETBE. The substituted aromatic amines were blended at 2.0 wt %. No manganese was added to these blends. The MON results listed in Tables 11–13 are average MON of two tests.

TABLE 11

MON Values for Methyl Substitutions on Aniline Ring

| | 80/20 vol % Wide boiling range alkylate + MTBE | | 80/20 vol % Wide boiling range alkylate + ETBE | |
|---|---|---|---|---|
| aromatic amine | MON | dMON* | MON | dMON* |
| Aniline | 96.3 | — | 97.3 | — |
| o-toluidine | 94.5 | −1.8 | 95.2 | −2.1 |
| m-toluidine | 96.8 | 0.5 | 97.4 | 0.1 |
| p-toluidine | 96.8 | 0.5 | 96.8 | −0.5 |

*Note: dMON = delta MON = difference between additive of interest and Aniline reference point.

TABLE 12

MON Values for di- and tri- methyl substitutions on Aniline Ring

| | 80/20 vol % Wide boiling range alkylate + MTBE | | 80/20 vol % Wide boiling range alkylate + ETBE | |
|---|---|---|---|---|
| aromatic amine | MON | dMON* | MON | dMON* |
| Aniline | 96.3 | — | 97.3 | — |
| 2,3-dimethyl Aniline | 93.8 | −2.6 | 94.2 | −3.1 |
| 2,4-dimethyl Aniline | 95.0 | −1.3 | 95.2 | −2.1 |
| 2,5-dimethyl Aniline | 93.9 | −2.4 | 95.3 | −2.1 |
| 2,6-dimethyl Aniline | 93.3 | −3.0 | 93.4 | −3.9 |
| 3,5-dimethyl Aniline | 95.7 | −0.6 | 96.7 | −0.6 |
| 2,4,6-trimethyl Aniline | 92.6 | −3.8 | 93.7 | −3.6 |

TABLE 13

MON Values for Alkyl Substitutions on Aniline's Amine

| | 80/20 vol % Wide boiling range alkylate + MTBE | | 80/20 vol % Wide boiling range alkylate + ETBE | |
|---|---|---|---|---|
| aromatic amine | MON | dMON* | MON | dMON* |
| Aniline | 96.3 | — | 97.3 | — |
| 4-ethyl Aniline | 96.1 | −0.3 | 97.5 | 0.2 |
| 4-n-butyl Aniline | 95.7 | −0.6 | 96.9 | −0.5 |
| n-methyl Aniline | 95.0 | −1.3 | 95.7 | −1.6 |
| n-ethyl Aniline | 91.9 | −4.4 | 91.9 | −5.4 |

It can be seen from Tables 11–13 that the aromatic amines which have a methyl substitution in the ortho- (or the 2 position) on the aromatic ring as well as the n-alkyl substitutions on the amine are not effective octane boosting additives for these two basefuels. However, the meta-ring position, (positions 3- and 5-) and the para-ring position, (position 4-) methyl substituted aromatic amines are generally more effective octane boosting additives for this basefuel with the exception of the p-toluidine in the ETBE/basefuel case. The relative MON increasing effectiveness of the different alkyl substituted aromatic amines exemplifies the importance of mapping the chemical oxidation reaction routes for the additives of interest relative to the MON test environment. Further data from these experiments are shown in FIGS. 4–15.

E. Determination of Non-linear Models for Identifying Aviation Fuel Compositions with Desirable MON, Supercharge, and Knock Cycle/Intensity Ratings To better characterize the performance of fuel formulations, the effects of various fuel formulations on MON, Supercharge and Knock Cycle/Intensity ratings were determined using statistically designed experiments. The subject fuel compositions were combinations of MTBE, aniline and manganese components and the same wide boiling range alkylate fuel as the previous designs. The three variable test ranges for these experiments were 20–30 vol % MTBE, 0–6 wt % aniline and 0–0.1 g/gal manganese. Anti-knock ratings of MON, Supercharge and Knock Cycle/Intensity ratings were measured at least in duplicate.

Table 14 shows the non-linear interactions of the fuel composition components on the Supercharge rating and average Knocking Cycles and average Knock Intensity per 400 consecutive engine cycles data. The eight fuel formulations shown represent the extremes of the ranges tested.

Statistical analysis shows an interaction between the MTBE and manganese terms in the equations for supercharge rating but only when aniline levels are low with respect to the domain tested. There is another significant interaction for supercharge rating which is that as MTBE increases the interaction between manganese and aniline becomes antagonistic. Also, the data analysis for Knock Intensity contains an antagonistic interaction between MTBE and aniline. The Knocking Cycles data demonstrates a three way interaction between the MTBE, manganese and aniline.

TABLE 14

Measured Octane Parameters with respect to Fuel Formulation

| MTBE (vol %) | Mn (g/gal) | Aniline (wt %) | MON | Supercharge Rating | Average Knocking Cycles/400 | Average Knock Intensity/400 |
|---|---|---|---|---|---|---|
| 20 | 0.00 | 0 | 95.4 | 115.5 | 121 | 49 |
| 20 | 0.00 | 6 | 97.6 | 140.2 | 12 | 32 |
| 20 | 0.10 | 0 | 95.6 | 118.1 | 68 | 40 |
| 20 | 0.10 | 6 | 98.0 | 142.5 | 4 | 24 |
| 30 | 0.00 | 0 | 96.2 | 114.1 | 66 | 35 |
| 30 | 0.00 | 6 | 98.3 | 143.9 | 2 | 33 |
| 30 | 0.10 | 0 | 97.4 | 133.5 | 13 | 33 |
| 30 | 0.10 | 6 | 99.3 | 144.5 | 2 | 20 |

Because of the above mentioned non-linear fuel composition interactions, neither MON nor supercharge ratings when considered individually will always predict the knock-free operation of the commercial Lycoming IO-360 aviation engine. (See Table 15). The Knocking Cycle and Knock Intensity data in Table 15 are the average of duplicate 400 cycle tests.

TABLE 15

Measured Octane Parameters with respect to Fuel Formulation (II)

| Fuel Number | MON | Supercharge Rating | Average Knocking Cycles/400 | Average Knock Intensity/400 |
|---|---|---|---|---|
| 1 | 98.4 | 134.9 | 17 | 30 |
| 2 | 98.5 | 142.2 | 0 | 0 |
| 3 | 96.5 | 136.1 | 0 | 0 |
| 4 | 96.3 | 115.1 | 73 | 35 |

The $R^2$ values between MON, Supercharge, Knocking Cycles and Knock Intensity are listed in Table 16.

TABLE 16

$R^2$ values for Knocking Cycles and Knock Intensity Predictions

| Combination | $R^2$ values |
|---|---|
| MON to predict Knocking Cycles* | .44 |
| MON to predict Knock Intensity* | .38 |

TABLE 16-continued

R² values for Knocking Cycles and Knock Intensity Predictions

| Combination | R² values |
|---|---|
| Supercharge to predict Knocking | .64 |
| Supercharge to predict Knock Intensity* | .82 |

Notes: (*) Outlying data points that were not representative of population were removed after statistical analyses.

Table 17 includes the references of pure isooctane as well as the industry standard leaded Avgas 100 Low Lead. For example, pure isooctane has a MON value of 100 by definition but knocks severely in the Lycoming IO-360 at its maximum potential knock operating condition. Addition of tetraethyllead (TEL) to isooctane is required to boost the supercharge rating sufficiently high to prevent auto-ignition in a commercial aircraft engine.

TABLE 17

Knock Data for Isooctane and Leaded Avgas 100 Low Lead

| Fuel | MON | Supercharge Rating | Knocking Cycles/400 | Knock Intensity/400 |
|---|---|---|---|---|
| Isooctane | 100 | 100 | 85 | Not Collected |
| 100 Low Lead | 105 | 131.2 | 0 | 0 |

Using centered & scaled units (s) for the fuel properties our equation for MON is:

$$MON=97.75+0.575*MTBE(s)+0.305*Mn(s)+1.135*Aniline(s)-0.485*Mn(s)^2.$$

Converting to actual units yields:

$$MON=92.95+0.115*MTBE+25.5*Mn+0.3783*Aniline-194*Mn^2.$$

No interactions were statistically significant.

Using centered and scaled units (s) for the fuel properties our equation for supercharge (SC) is.

$$SC = 140.008 + 2.325*MTBE(s) + 3.9*Mn(s) + 11.715*Aniline(s) + 1.89375*MTBE(s)*Mn(s) - 2.39375*Mn(s)*Aniline(s) - 2.30625*MTBE(s)*Mn(s)*Aniline(s) - 8.653*Aniline(s)^2.$$

Converting to actual units yields:

$$SC = 122.72 - 0.375*MTBE - 294.125*Mn + 6.628*Aniline + 16.8*MTBE*Mn + 0.15375*MTBE*Aniline + 60.917*Mn*Aniline - 3.075*MTBE*Mn*Aniline - 0.9614815*Aniline^2$$

Looking at the equation in centered and scaled units, we see that the interaction between MTBE and Mn is synergistic (coefficient same sign as coefficients for individual effects of MTBE*Mn). But, because of the presence of the 3-way interaction between MTBE, Mn, and Aniline, the size of the MTBE*Mn interaction actually depends on the level of aniline. At the low level of aniline, the MTBE*Mn interaction is synergistic, but as the aniline level increases, the MTBE*Mn interaction becomes less and less synergistic until it becomes basically zero at the high aniline level (if anything, it is antagonistic at this point). Thus, there is a synergism between MTBE and Mn, but generally only at low levels of aniline.

A similar description can be used for the Mn*Aniline interaction, where the size of this interaction depends on the MTBE level. At low levels of MTBE, the Mn*Aniline interaction is essentially zero, but as the MTBE level increases the Mn*Aniline interaction becomes more and more agonistic. Table 18 below illustrates the above concepts.

TABLE 18

| MTBE (vol %) | Mn (g/gal) | Aniline (wt %) | Actual SC | Predicted SC | Expected SC[1] |
|---|---|---|---|---|---|
| 20 | 0.00 | 0 | 122.2, 108.7 | 115.2 | |
| 20 | 0.10 | 0 | 116.8, 119.4 | 119.4 | |
| 30 | 0.00 | 0 | 113.0, 115.1 | 111.5 | |
| 30 | 0.10 | 0 | 132.1, 134.9 | 132.5 | 115.7 |
| 20 | 0.00 | 6 | 137.6, 142.8 | 138.8 | |
| 20 | 0.10 | 6 | 142.7, 142.8 | 142.7 | |
| 30 | 0.00 | 6 | 143.8, 143.9 | 144.3 | |
| 30 | 0.10 | 6 | 143.9, 145.1 | 146.5 | 148.2 |

[1]- This is the expected SC value if there was no interaction, that is if the effects of each of the fuel components were additive.

Using centered and scaled units (s) for the fuel properties our equation for Knock Intensity (KInt) is:

$$KInt=26.5-2.138719*MTBE(s)-1.905819*Mn(s)-5.877127*Aniline(s)+2.477696*MTBE(s)*Aniline(s)+2.711142*Mn(s)^2+2.780729*Aniline(s)^2$$

Converting to actual units yields:

$$KInt=62.9-0.923283*MTBE-146.56206*Mn-7.9423549*Aniline+0.1651797*MTBE*Aniline+1084.4568*Mn^2+0.3089699*Aniline^2$$

Again looking at the equation in the centered and scaled units, we see that the MTBE*Aniline interaction is antagonistic. Also, note that this interaction does not depend on the Mn level because there is no 3-way interaction in the model. The following Table 19 illustrates this interaction.

TABLE 19

| MTBE (vol %) | Mn (g/gal) | Aniline (wt %) | Actual Knock Int. | Predicted Knock Int. | Expected Knock Int.[1] |
|---|---|---|---|---|---|
| 20 | 0.00 | 0 | 52.0, 48.1, 38.0 | 44.4 | |
| 20 | 0.00 | 6 | 36.1, 27.3, 26.0 | 27.7 | |
| 30 | 0.00 | 0 | 34.4, 35.3 | 35.2 | |
| 30 | 0.00 | 6 | 25.7, 40.0 | 28.4 | 18.5 |
| 20 | 0.10 | 0 | 39.4, 40.9, 38.7 | 40.6 | |
| 20 | 0.10 | 6 | 19.0, 28.4, 19.0 | 23.9 | |
| 30 | 0.10 | 0 | 37.6, 30.0, 28.0 | 31.4 | |
| 30 | 0.10 | 6 | 21.0, 19.0 | 24.6 | 14.7 |

[1]- This is the expected Knock Intensity value if there was no interaction, that is if the effects of each of the fuel components were additive.

It should be pointed out that knock intensity values below 20 cannot be distinguished from each other, so the antagonistic effect of the MTBE*Aniline interaction may not be quite so significant at the high level of Mn (since the expected value under the assumption of no interaction is 14.7 and the actual values were 21.0 and 19.0).

Using centered and scaled units (s) for the fuel properties, our equation for number of Knocking Cycles (Cycles) is:

$Y=\ln(\text{Cycles}+1)=1.529878-0.43339*MTBE(s)-0.376319*Mn(s)-1.469152*\text{Aniline}(s)+0.368344*MTBE(s)*Mn(s)*\text{Aniline}(s)+0.732549*\text{Aniline}(s)^2.$ Converting to actual units yields:

$Y = \ln(\text{Cycles}+1) = 4.4331281 - 0.0130092*MTBE +$
$29.308018*Mn - 0.3641767*\text{Aniline} - 1.4733759*MTBE*Mn -$
$0.0245563*MTBE*\text{Aniline} - 12.278133*Mn*\text{Aniline} +$
$0.4911253*MTBE*Mn*\text{Aniline} + 0.0813943*\text{Aniline}^2.$ In either case, the predicted number of knocking cycles is equal to $e^Y - 1$.

This variable was analyzed on the natural log (ln) scale because it was observed that the variability was a function of mean level. Analyzing the data on the ln scale causes the variability to be more constant across mean levels, which is necessary for the statistical tests performed to be valid. Also, since some observations had values of zero for number of knocking cycles (the natural log of zero cannot be calculated), 1 was added to every observation so that the ln transformation could be used. Thus, 1 must be subtracted from Y above to get back to the original units.

Because of the presence of the 3-way interaction in the model and no 2-way interactions, the 3-way interaction can be interpreted in 3 ways. We could say that there is a synergistic interaction between MTBE and Mn at low levels of aniline and an antagonistic interaction at high levels of aniline. This description holds for all pairs of fuel properties.

The following Table 20 describes the MTBE*Mn interaction being synergistic at low levels of aniline and being antagonistic at high levels of aniline

TABLE 20

| MTBE (vol %) | Mn (g/gal) | Aniline (wt %) | Avg. No. of Knocking Cycles | Pred. No. of Knocking Cycles | Expected No. of Knocking Cycles[1] |
|---|---|---|---|---|---|
| 20 | 0.00 | 0 | 178.5, 93.0, 28.0 | 63.9 | |
| 20 | 0.10 | 0 | 78.5, 48.0, 71.5 | 62.9 | |
| 30 | 0.00 | 0 | 56.5, 73.0 | 56.0 | |
| 30 | 0.10 | 0 | 17.0, 0.8, 17.0 | 11.9 | 55.1 |
| 20 | 0.00 | 6 | 13.0, 15.5, 0.5 | 6.2 | |
| 20 | 0.10 | 6 | 0.0, 5.5, 0.0 | 0.6 | |
| 30 | 0.00 | 6 | 1.5, 0.5 | 0.4 | |
| 30 | 0.10 | 6 | 1.0, 0.0 | 0.4 | 0.0 |

[1]-This is the expected avg. No. of knocking cycles value if there was no interaction, that is if the effects of each of the fuel components were additive.

Note that at the high aniline level, the reason for the antagonistic MTBE*Mn interaction is that the number of knocking cycles cannot be reduced to a value lower than zero. Increasing Mn to 0.10 lowers the number of knocking cycles to almost zero and increasing MTBE to 30 also lowers the number of knocking cycles to almost zero. Therefore, increasing both Mn and MTBE at the same time cannot reduce the number of knocking cycles any more.

Using centered and scaled units (s) for the fuel properties our equation for the number of Knocking Cycles is:

$\text{Cycles} = 4.462241 - 9.166427*MTBE(s) -$
$7.93772*Mn(s) - 26.077604*\text{Aniline}(s) +$
$8.742241*MTBE(s)*\text{Aniline}(s) + 8.491223*Mn(s)*\text{Aniline}(s) +$
$5.167309*MTBE(s)*Mn(s)*\text{Aniline}(s) + 24.483337*\text{Aniline}(s)^2.$ Converting to actual units yields:

$\text{Cycles} = 135.2 - 2.5482718*MTBE + 188.15204*Mn -$
$33.803388*\text{Aniline} - 20.669236*MTBE*Mn +$
$0.2383288*MTBE*\text{Aniline} - 115.63548*Mn*\text{Aniline} +$
$6.8897453*MTBE*Mn*\text{Aniline} + 2.7203708*\text{Aniline}^2.$ In this case, the only synergistic interaction is between MTBE and Mn at low aniline levels. All other interactions are antagonistic The MTBE*Mn synergism at low aniline levels and antagonism at high aniline levels is shown below in Table 21.

TABLE 21

| MTBE (vol %) | Mn (g/gal) | Aniline (wt %) | Avg. No. of Knocking Cycles | Pred. # of Knocking Cycles | Expected # of Knocking Cycles[a] |
|---|---|---|---|---|---|
| 20 | 0.00 | 0 | 178.5[b], 93.0, 28.0[b] | 84.2 | |
| 20 | 0.10 | 0 | 78.5, 48.0, 71.5 | 61.7 | |
| 30 | 0.00 | 0 | 56.5, 73.0 | 58.7 | |
| 30 | 0.10 | 0 | 17.0, 0.8, 17.0 | 15.5 | 36.2 |
| 20 | 0.00 | 6 | 13.0, 15.5, 0.5 | 7.9 | |
| 20 | 0.10 | 6 | 0.0, 5.5, 0.0 | 0.0 | |
| 30 | 0.00 | 6 | 1.5, 0.5 | 0.0 | |
| 30 | 0.10 | 6 | 1.0, 0.0 | 8.2 | 0.0 |

[a]- This is the expected avg. no. of knocking cycles value if there was no interaction, that is if the effects of each of the fuel components were additive.
[b]- These observations were not included in the analyses.

Further data from these experiments are shown in FIGS. 16–30.

The testing and equation fitting variability of the second set of experimentally designed cubes is demonstrated in Tables 22 and 23. For the predicted performance parameter listed in Table 22, the 95% total variability is a combination of engine measurement and fuel blending variabilities. Table 22 also shows the performance parameter engine measurement and fuel blending variability in terms of standard deviation and total variability calculated at the 95% confidence limit.

TABLE 22

| Variability Analysis for Second Cube Sets | | |
|---|---|---|
| Performance Parameter | Standard Deviation | 95% Total Variability |
| MON | 0.69 | 2.07 |
| Performance Number | 3.93 | 11.73 |
| Knock Intensity | 7.04 | 19.70 |
| Knocking Cycles (ln Scale) | 1.15 | 3.27 |
| Knocking cycles (linear Scale) | 18.6 | 52.60 |

Total variability, as used here, is defined as it is in ASTM Methods—for two single measurements, the maximum difference two numbers can have and still be considered equal. However, variability as used here is neither purely repeatability nor reproducibility, but is somewhere between the two definitions. The accuracy and variability for the equation fitting process of the performance parameters is shown in Table 23.

TABLE 23

Equation Fitting Variability for Second Cube Set

| Performance Parameter | $R^2$ Value | Root Mean Squared Error | Average Error |
|---|---|---|---|
| MON | 76.8 | 0.63 | 0.47 |
| Performance Number | 91.2 | 3.99 | 2.50 |
| Knock Intensity | 60.5 | 5.40 | 3.80 |
| Knocking Cycles (in small "L" Scale) | 74.2 | 0.83 | 0.60 |
| Knocking Cycles (linear Scale) | 89.1 | 9.30 | 7.10 |

Other features, advantages and embodiments of the invention disclosed herein will be readily apparent to those exercising ordinary skill after reading the foregoing disclosure. In this regard, while specific embodiments of the invention have been described in detail, variations and modifications of these embodiments can be effected without departing from the spirit and scope of the invention as described and claimed.

What is claimed is:

1. A method for testing the performance of an unleaded Avgas composition comprising:

(a) running an aviation engine with an Avgas at maximum knocking conditions, (b) collecting pressure trace data of continuous engine cycles with pressure transducers attached to the cylinders, (c) filtering and transforming the data, and (d) determining the number of knocking cycles within a predetermined number of continuous engine cycles; and (e) rating the performance of the Avgas based on knocking cycles, wherein an acceptable performance level is designated for an Avgas averaging fewer than 50 knocking events per 400 cycles.

2. The method of claim 1, wherein the aviation engine is a Textron Lycoming IO-360 engine.

3. The method of claim 1, wherein the Avgas composition comprises a wide boiling range alkylate basefuel and one or more additives.

4. The method according to claim 1, wherein the aviation engine is run at 2700 rpm.

5. The method according to claim 4, wherein the aviation engine is run with a wide open throttle.

6. The method according to claim 5, wherein the aviation engine is run at an equivalence ratio of about 1.12.

* * * * *

UNITED STATES PATENT AND TRADEMARK OFFICE
CERTIFICATE OF CORRECTION

PATENT NO. : 5,962,775

DATED : October 5, 1999

INVENTOR(S) : Liiva et al.

Page 1 of 2

It is certified that error appears in the above-identified patent and that said Letters Patent is hereby corrected as shown below:

column 4, line 41, in TABLE 5, delete
"30　96.6　　97.5　　99.4　　161.3　"
and replace with
--30　96.6　　97.5　　99.4　　101.3　--.

, column 6, line 48, in TABLE 10, delete
"ETBE + Aniline　　74.5　　1.29　　0.85　"
and replace with
--ETBE + Aniline　　74.5　　1.29　　0.88　--.

column 10, line 8, delete "agonistic" and replace with --antagonistic--.

, column 10, line 23, on the footnote of TABLE 18, delete "eacb" and replace with --each--.

UNITED STATES PATENT AND TRADEMARK OFFICE
CERTIFICATE OF CORRECTION

PATENT NO. : 5,962,775

DATED : October 5, 1999

Page 2 of 2

INVENTOR(S) : Liiva et al.

It is certified that error appears in the above-identified patent and that said Letters Patent is hereby corrected as shown below:

column 11, lines 17, 19 and 24, delete "1n" and replace with --ln-- (delete the number one and replace with the lowercase letter L).

column 12, line 21, delete "antagonistic" and replace with --antagonistic.-- (add a period at the end of the sentence).

column 12, line 26, in TABLE 21, in the table heading row, delete both occurrences of "#" (in the last two columns of the table), and replace with --No.--.

Signed and Sealed this

Twenty-fifth Day of April, 2000

Attest:

Q. TODD DICKINSON

*Attesting Officer*  *Director of Patents and Trademarks*